(12) United States Patent
Luo et al.

(10) Patent No.: US 10,647,968 B2
(45) Date of Patent: May 12, 2020

(54) ENDOSTATIN MUTANTS WITH MUTATIONS AT ATP BINDING SITES

(75) Inventors: Yongzhang Luo, Beijing (CN); Peng Liu, Beijing (CN); Xinan Lu, Beijing (CN); Yang Chen, Beijing (CN); Yan Fu, Beijing (CN); Guodong Chang, Beijing (CN); Daifu Zhou, Beijing (CN)

(73) Assignees: Tsinghua University, Beijing (CN); Beijing Protgen Ltd., Beijing (CN)

( * ) Notice: Subject to any disclaimer, the term of this patent is extended or adjusted under 35 U.S.C. 154(b) by 252 days.

(21) Appl. No.: 14/343,694

(22) PCT Filed: Sep. 10, 2012

(86) PCT No.: PCT/CN2012/081210
§ 371 (c)(1),
(2), (4) Date: Jun. 26, 2014

(87) PCT Pub. No.: WO2013/034116
PCT Pub. Date: Mar. 14, 2013

(65) Prior Publication Data
US 2014/0308263 A1    Oct. 16, 2014
US 2015/0197733 A9    Jul. 16, 2015

(30) Foreign Application Priority Data

Sep. 9, 2011 (CN) .......................... 2011 1 0280441

(51) Int. Cl.
*A61K 38/18* (2006.01)
*C12N 9/14* (2006.01)
*C07K 14/475* (2006.01)
*C12Q 1/00* (2006.01)
*A61K 47/60* (2017.01)

(52) U.S. Cl.
CPC ................ *C12N 9/14* (2013.01); *A61K 38/18* (2013.01); *A61K 47/60* (2017.08); *C07K 14/475* (2013.01); *C12Q 1/00* (2013.01)

(58) Field of Classification Search
None
See application file for complete search history.

(56) References Cited

U.S. PATENT DOCUMENTS

| 7,339,027 B2 | 3/2008 | Chen | |
| 2010/0285103 A1* | 11/2010 | Luo | A61K 38/363 424/450 |
| 2010/0305303 A1* | 12/2010 | Xu | A61K 38/08 530/322 |
| 2011/0092441 A1 | 4/2011 | Jo et al. | |

FOREIGN PATENT DOCUMENTS

| CN | 1324818 A | 12/2001 |
| CN | 101002946 A | 7/2007 |
| CN | 101256139 A | 9/2008 |

OTHER PUBLICATIONS

Yuan, S., "Studies on the Mechanism of Human Endostatin-Induced Endothelial Cell Apoptosis," China Doctoral Dissertions Full-Text Database (E-Journal), Medicine & Hygiene, 2009, No. 8, Aug. 15, 2009, (English abstract included), 125 pages.
International Search Report, PCT/CN2012/081210 dated Dec. 20, 2012, 8 pages.

* cited by examiner

*Primary Examiner* — Mark Halvorson
(74) *Attorney, Agent, or Firm* — Rothwell, Figg, Ernst & Manbeck, P.C.

(57) ABSTRACT

The present invention discloses a new anti-tumor medicament comprising a mutant of endostatin. The mutant comprises a mutation in the ATP-binding site of endostatin and has a decreased ATPase activity and an increased anti-angiogenesis activity.

6 Claims, 24 Drawing Sheets
Specification includes a Sequence Listing.

```
endostatin_[homo_sapiens].seq    H HDFQPVLHLVALN PLSGGMRGIRGADFQCFQQARAV    40
endostatin_[Mus_musculus].seq    HTHDEQPVLHLVALN PLSGGMRGIRGADFQCFQQARAV    40
Consensus                        h h dfqpvlhlvaln plsggmrgirgadfqcfqqarav endostatin_[homo_sapiens].seq    GL GTERAFLSSRLQDLYSIVRRADRA VPIVNLKDE L    80
endostatin_[Mus_musculus].seq    GLSGTERAFLSSRLQDLYSIVRRADRSVPIVNLKDE S    80
Consensus                        gl gtfraflssrlqdlysivrradr  vpivnlkde l endostatin_[homo_sapiens].seq    PSW  LFSGS G L PGARIFSFDG DVLRHP WPQKSVW   120
endostatin_[Mus_musculus].seq    PSWG LFSGS GCL PGARIFSFDG DVLRHP WPQKSVW   120
Consensus                        psw  lfsgs g l pgarifsfdg dvlrhp wpqksvw endostatin_[homo_sapiens].seq    HGSDP GRRL ESYCETWRTE  ATGQASSLL GRLL Q    160
endostatin_[Mus_musculus].seq    HGSDP GRRL ESYCETWRTETT ATGQASSLL GRLL Q   160
Consensus                        hgsdp grrl esycetwrte   atgqassll grll q endostatin_[homo_sapiens].seq    AASCH YIVLCIENSFMT S                       183
endostatin_[Mus_musculus].seq    AASCH YIVLCIENSFMT S                       183
Consensus                        aasch yivlciensfmt
```

Figure 1

A
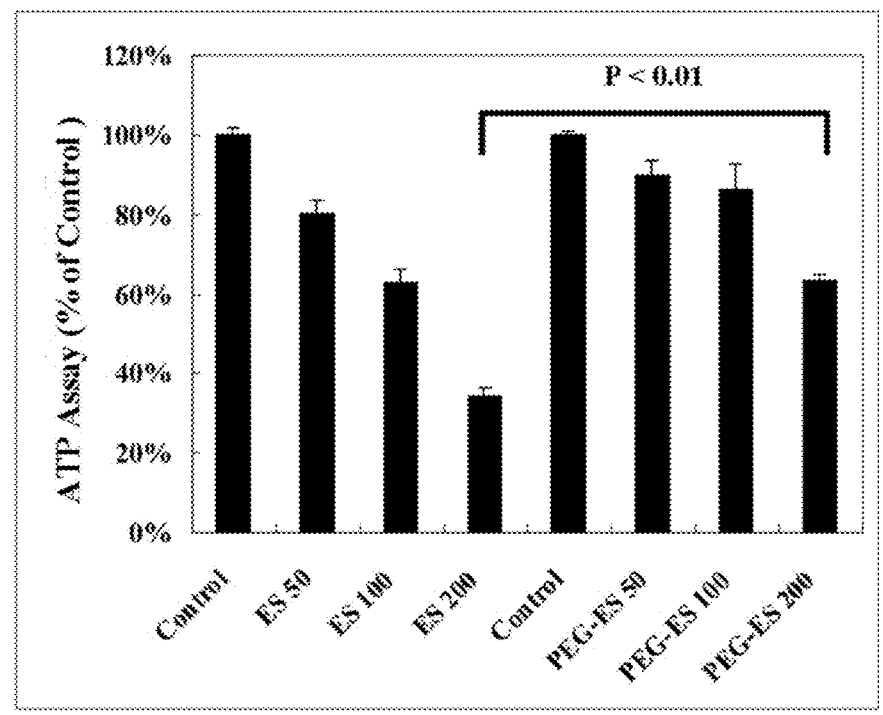
B
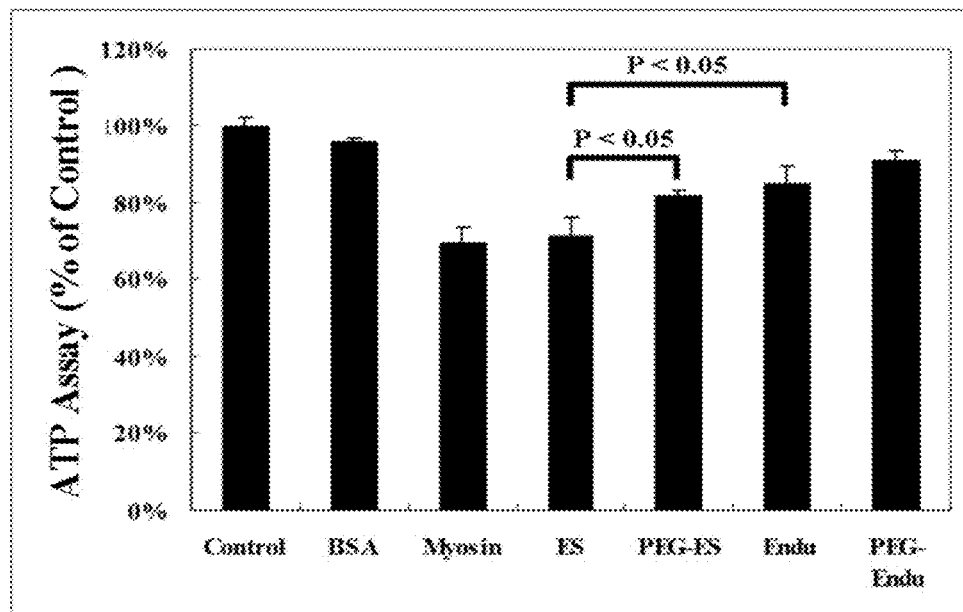
Figure 4

A
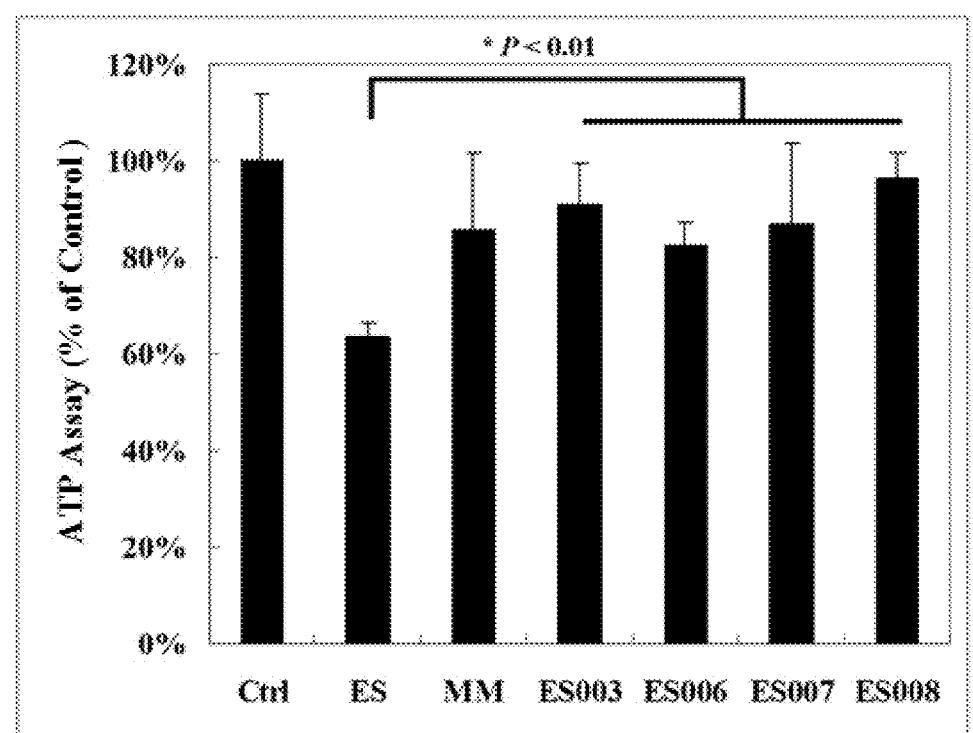
B
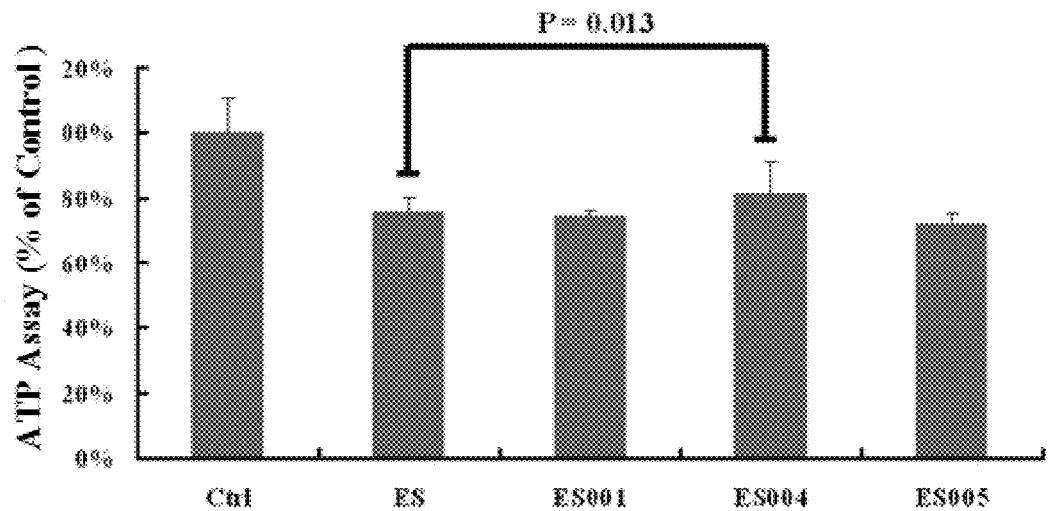
Figure 7

A
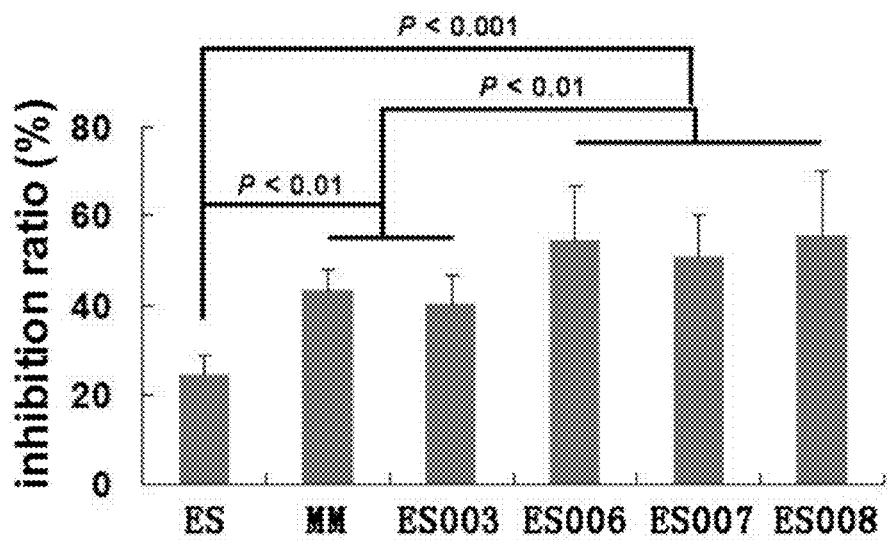
B
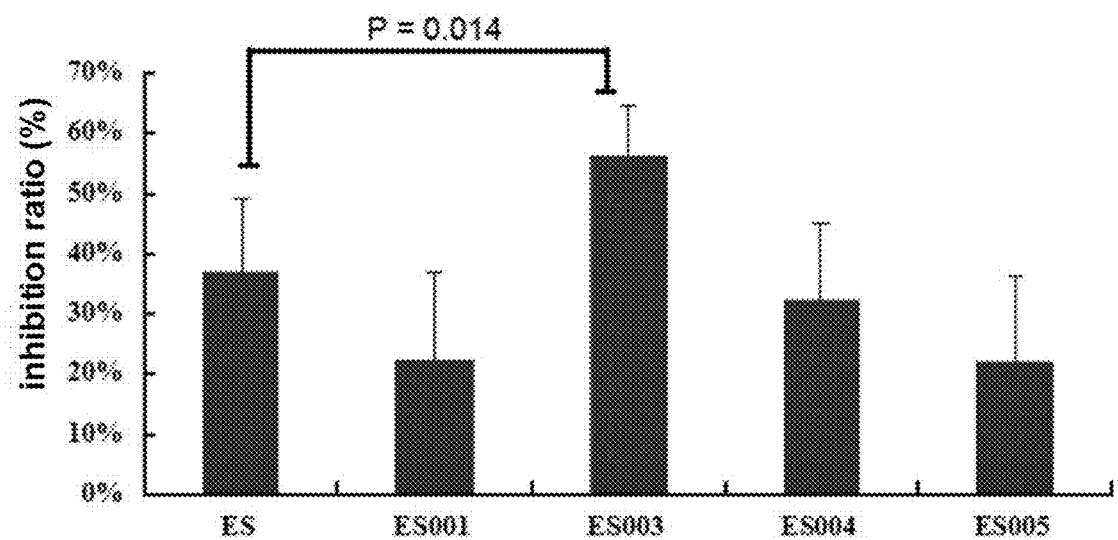
Figure 8

A
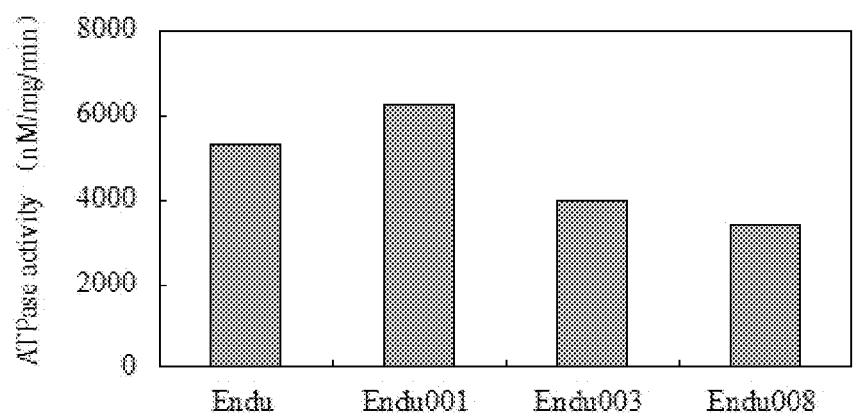
B
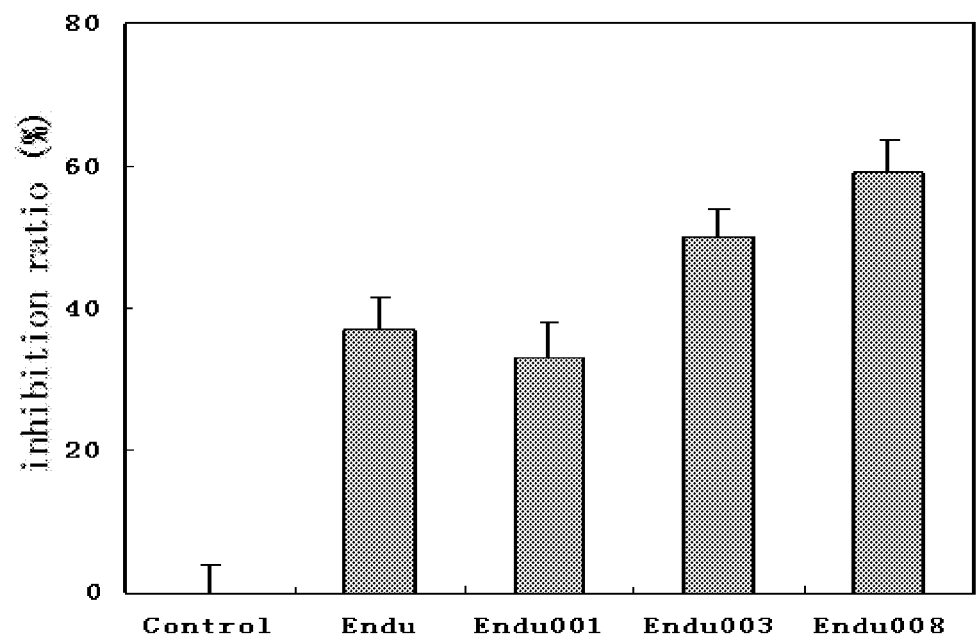
Figure 9

HSHRDFQPVLHLVALNSPLSGGMRGIRGADFQCFQQAR
AVGLAGTFRAFLSSRLQDLYSIVRRADRAAVPIVNLKDELL
FPSWEALFSGSEGPLKPGARIFSFDGKDVLRHPTWPQKSV
WHGSDPNGRRLTESYCETWRTEAPSATGQASSLLGGRLL
GQSAASCHHAYIVLCIENSFMTASK

Figure 10

(M)HSHRDFQPVLHLVALNSPLSGGMRGIRGADFQCFQQAR
AVGLAGTFRAFLSSRLQDLYSIVRRADRAAVPIVNLKDELL
FPSWEALFSGSEGPLKPGARIFSFDGKDVLRHPTWPQKSV
WHGSDPNGRRLTESYCETWRTEAPSATGQASSLLGGRLL
GQSAASCHHAYIVLCIENSFMTASK

Figure 11

(M)DFQPVLHLVALNSPLSGGMRGIRGADFQCFQQARAVGL
AGTFRAFLSSRLQDLYSIVRRADRAAVPIVNLKDELLFPSW
EALFSGSEGPLKPGARIFSFDGKDVLRHPTWPQKSVWHG
SDPNGRRLTESYCETWRTEAPSATGQASSLLGGRLLGQS
AASCHHAYIVLCIENSFMTASK

Figure 12

(M)GGSHHHHHHSHRDFQPVLHLVALNSPLSGGMRGIRGAD
FQCFQQARAVGLAGTFRAFLSSRLQDLYSIVRRADRAAVP
IVNLKDELLFPSWEALFSGSEGPLKPGARIFSFDGKDVLRH
PTWPQKSVWHGSDPNGRRLTESYCETWRTEAPSATGQAS
SLLGGRLLGQSAASCHHAYIVLCIENSFMTASK

Figure 13

(M)HSHRDFQPVLHLVALNSPLSGGMRGIRGADFQCFQQAR
AVGLAGTFRAFLSSRLQDLYSIVRRADRAAVPIVNLKDELL
FPSWEALFSGSEGPLRPGARIFSFDGKDVLRHPTWPQKSV
WHGSDPNGRRLTESYCETWRTEAPSATGQASSLLGGRLL
GQSAASCHHAYIVLCIENSFMTASK

Figure 14

(M)HSHRDFQPVLHLVALNSPLSGGMRGIRGADFQCFQQAR
AVGLAGTFRAFLSSRLQDLYSIVRRADRAAVPIVNLKDELL
FPSWEALFSASEGPLKPGARIFSFDGKDVLRHPTWPQKSV
WHGSDPNGRRLTESYCETWRTEAPSATGQASSLLGGRLL
GQSAASCHHAYIVLCIENSFMTASK

Figure 15

(M)HSHRDFQPVLHLVALNSPLSGGMRGIRGADFQCFQQAR
AVGLAGTFRAFLSSRLQDLYSIVRRADRAAVPIVNLKDELL
FPSWEALFSGSEAPLRPGARIFSFDGKDVLRHPTWPQKSV
WHGSDPNGRRLTESYCETWRTEAPSATGQASSLLGGRLL
GQSAASCHHAYIVLCIENSFMTASK

Figure 16

(M)HSHRDFQPVLHLVALNSPLSGGMRGIRGADFQCFQQAR
AVGLAGTFRAFLSSRLQDLYSIVRRADRAAVPIVNLKDELL
FPSWEALFSASEAPLRPGARIFSFDGKDVLRHPTWPQKSV
WHGSDPNGRRLTESYCETWRTEAPSATGQASSLLGGRLL
GQSAASCHHAYIVLCIENSFMTASK

Figure 17

(M)HSHRDFQPVLHLVALNSPLSGGMRGIRGADFQCFQQAR
AVGLAGTFRAFLSSRLQDLYSIVRRADRAAVPIVNLKDELL
FPSWEALFSGSEAPLKPGARIFSFDGKDVLRHPTWPQKSV
WHGSDPNGRRLTESYCETWRTEAPSATGQASSLLGGRLL
GQSAASCHHAYIVLCIENSFMTASK

Figure 18

(M)HSHRDFQPVLHLVALNSPLSGGMRGIRGADFQCFQQAR
AVGLAGTFRAFLSSRLQDLYSIVRRADRAAVPIVNLKDELL
FPSWEALFSASKAPLQPGARIFSFDGKDVLRHPTWPQKSV
WHGSDPNGRRLTESYCETWRTEAPSATGQASSLLGGRLL
GQSAASCHHAYIVLCIENSFMTASK

Figure 19

(M)HSHRDFQPVLHLVALNSPLSGGMRGIRGADFQCFQQAR
AVGLAGTFRAFLSSRLQDLYSIVRRADRAAVPIVNLKDELL
FPSWEALFSGSQGQLQPGARIFSFDGKDVLRHPTWPQKSV
WHGSDPNGRRLTESYCETWRTEAPSATGQASSLLGGRLL
GQSAASCHHAYIVLCIENSFMTASK

Figure 20

(M)GGSHHHHHHSHRDFQPVLHLVALNSPLSGGMRGIRGAD
FQCFQQARAVGLAGTFRAFLSSRLQDLYSIVRRADRAAVP
IVNLKDELLFPSWEALFSGSEGPLRPGARIFSFDGKDVLRH
PTWPQKSVWHGSDPNGRRLTESYCETWRTEAPSATGQAS
SLLGGRLLGQSAASCHHAYIVLCIENSFMTASK

Figure 21

(M)GGSHHHHHHSHRDFQPVLHLVALNSPLSGGMRGIRGAD
FQCFQQARAVGLAGTFRAFLSSRLQDLYSIVRRADRAAVP
IVNLKDELLFPSWEALFSASEGPLKPGARIFSFDGKDVLRH
PTWPQKSVWHGSDPNGRRLTESYCETWRTEAPSATGQAS
SLLGGRLLGQSAASCHHAYIVLCIENSFMTASK

Figure 22

(M)GGSHHHHHHSHRDFQPVLHLVALNSPLSGGMRGIRGAD
FQCFQQARAVGLAGTFRAFLSSRLQDLYSIVRRADRAAVP
IVNLKDELLFPSWEALFSGSQGQLQPGARIFSFDGKDVLRH
PTWPQKSVWHGSDPNGRRLTESYCETWRTEAPSATGQAS
SLLGGRLLGQSAASCHHAYIVLCIENSFMTASK

Figure 23

MHSHMDFQPVLHLVALNSPLSGGMRG
IRGADFQCFQQARAVGLAGTFRAFLSS
RLQDLYSIVRRADRAAVPIVNLKDELLF
PSWEALFSGSEGPLKPGARIFSFDGKD
VLRHPTWPQKSVWHGSDPNGRRLTES
YCETWRTEAPSATGQASSLLGGRLLGQ
SAASCHHAYIVLCIENSFMTASK

Figure 24

MHSHQDFQPVLHLVALNSPLSGGMRG
IRGADFQCFQQARAVGLAGTFRAFLSS
RLQDLYSIVRRADRAAVPIVNLKDELLF
PSWEALFSGSEGPLKPGARIFSFDGKD
VLRHPTWPQKSVWHGSDPNGRRLTES
YCETWRTEAPSATGQASSLLGGRLLGQ
SAASCHHAYIVLCIENSFMTASK

Figure 25

MHSHQDFQPVLHLVALNSPLSGGMRG
IRGADFQCFQQARAVGLAGTFRAFLSS
RLQDLYSIVRRADRAAVPIVNLKDELLF
PSWEALFSGSQGQLQPGARIFSFDGKD
VLRHPTWPQKSVWHGSDPNGRRLTES
YCETWRTEAPSATGQASSLLGGRLLGQ
SAASCHHAYIVLCIENSFMTASK

Figure 26

MDFQPVLHLVALNSPLSGGMRGIRGA
DFQCFQQARAVGLAGTFRAFLSSRLQD
LYSIVRRADRAAVPIVNLKDELLFPSWE
ALFSGSEGPLKSPGARIFSFDGKDVLRH
PTWPQKSVWHGSDPNGRRLTESYCET
WRTEAPSATGQASSLLGGRLLGQSAAS
CHHAYIVLCIENSFMTASK

Figure 27

MDFQPVLHLVALNSPLSGGMRGIRGA
DFQCFQQARAVGLAGTFRAFLSSRLQD
LYSIVRRADRAAVPIVNLKDELLFPSWE
ALFSGSEGPLKTPGARIFSFDGKDVLRH
PTWPQKSVWHGSDPNGRRLTESYCET
WRTEAPSATGQASSLLGGRLLGQSAAS
CHHAYIVLCIENSFMTASK

Figure 28

MHSHRDFQPVLHLVALNSPLSGGMRG
IRGADFQCFQQARAVGLAGTFRAFLSS
RLQDLYSIVRRADRAAVPIVNLKDELLF
PSWEALFSGSEGPLKSPGARIFSFDGKD
VLRHPTWPQKSVWHGSDPNGRRLTES
YCETWRTEAPSATGQASSLLGGRLLGQ
SAASCHHAYIVLCIENSFMTASK

Figure 29

MHSHRDFQPVLHLVALNSPLSGGMRG
IRGADFQCFQQARAVGLAGTFRAFLSS
RLQDLYSIVRRADRAAVPIVNLKDELLF
PSWEALFSGSEGPLKTPGARIFSFDGKD
VLRHPTWPQKSVWHGSDPNGRRLTES
YCETWRTEAPSATGQASSLLGGRLLGQ
SAASCHHAYIVLCIENSFMTASK

Figure 30

MHSHRDFQPVLHLVALNSPLSGGMRG
IRGADFQCFQQARAVGLAGTFRAFLSS
RLQDLYSIVRRADRAAVPIVNLKDELLF
PSWEALFSGSEGPLKPGARIFSFDGKD
VLRHPTWPQKSVWHGSDPNGRRLTES
YCETWRTEAPSATGQASSLLGGRLLGQ
SAASCHHAYIVLCIENSFM

Figure 31

MHSHRDFQPVLHLVALNSPLSGGMRG
IRGADFQCFQQARAVGLAGTFRAFLSS
RLQDLYSIVRRADRAAVPIVNLKDELLF
PSWEALFSSEPLQPGARIFSFDGKDVLR
HPTWPQKSVWHGSDPNGRRLTESYCE
TWRTEAPSATGQASSLLGGRLLGQSAA
SCHHAYIVLCIENSFMTASK

Figure 32

MHSHQDFQPVLHLVALNSPLSGGMRG
IRGADFQCFQQARAVGLAGTFRAFLSS
RLQDLYSIVRRADRAAVPIVNLKDELLF
PSWEALFSSEGPLKPGARIFSFDGKDVL
RHPTWPQKSVWHGSDPNGRRLTESYC
ETWRTEAPSATGQASSLLGGRLLGQSA
ASCHHAYIVLCIENSFMTASK

Figure 33

MHSHQDFQPVLHLVALNSPLSGGMRG
IRGADFQCFQQARAVGLAGTFRAFLSS
RLQDLYSIVRRADRAAVPIVNLKDELLF
PSWEALFSSEPLKPGARIFSFDGKDVLR
HPTWPQKSVWHGSDPNGRRLTESYCE
TWRTEAPSATGQASSLLGGRLLGQSAA
SCHHAYIVLCIENSFMTASK

Figure 34

MHSHQDFQPVLHLVALNSPLSGGMRG
IRGADFQCFQQARAVGLAGTFRAFLSS
RLQDLYSIVRRADRAAVPIVNLKDELLF
PSWEALFSSEGPLQPGARIFSFDGKDV
LRHPTWPQKSVWHGSDPNGRRLTESY
CETWRTEAPSATGQASSLLGGRLLGQS
AASCHHAYIVLCIENSFMTASK

Figure 35

MHSHRDFQPVLHLVALNSPLSGGMRG
IRGADFQCFQQARAVGLAGTFRAFLSS
RLQDLYSIVRRADRAAVPIVNLKDELLF
PSWEALFSSEGPLKPGARIFSFDGRDVL
RHPTWPQRSVWHGSDPNGRRLTESYC
ETWRTEAPSATGQASSLLGGRLLGQSA
ASCHHAYIVLCIENSFMTASR

Figure 36

MHSHRDFQPVLHLVALNSPLSGGMRG
IRGADFQCFQQARAVGLAGTFRAFLSS
RLQDLYSIVRRADRAAVPIVNLRDELLF
PSWEALFSGSQGQLQPGARIFSFDGRD
VLRHPTWPQKSVWHGSDPNGRRLTES
YCETWRTEAPSATGQASSLLGGRLLGQ
SAASCHHAYIVLCIENSFMTASR

Figure 37

MHSHRDFQPVLHLVALNSPLSGGMRG
IRGADFQCFQQARAVGLAGTFRAFLSS
RLQDLYSIVRRADRAAVPIVNLKDELLF
PSWEALFSGESGAGRTPGARIFSFDGK
DVLRHPTWPQKSVWHGSDPNGRRLTE
SYCETWRTEAPSATGQASSLLGGRLLG
QSAASCHHAYIVLCIENSFMTASK

Figure 38

MHSHRDFQPVLHLVALNSPLSGGMRG
IRGADFQCFQQARAVGLAGTFRAFLSS
RLQDLYSIVRRADRAAVPIVNLRDELLF
PSWEALFSSEGPLKPGARIFSFDGRDVL
RHPTWPQRSVWHGSDPNGRRLTESYC
ETWRTEAPSATGQASSLLGGRLLGQSA
ASCHHAYIVLCIENSFMTASR

Figure 39

MHSHRDFQPVLHLVALNSPLSGGMRG
IRGADFQCFQQARAVGLAGTFRAFLSS
RLQDLYSIVRRADRAAVPIVNLRDELLF
PSWEALFSASEGPLKPGARIFSFDGRD
VLRHPTWPQRSVWHGSDPNGRRLTES
YCETWRTEAPSATGQASSLLGGRLLGQ
SAASCHHAYIVLCIENSFMTASR

Figure 40

MHSHRDFQPVLHLVALNSPLSGGMRG
IRGADFQCFQQARAVGLAGTFRAFLSS
RLQDLYSIVRRADRAAVPIVNLRDELLF
PSWEALFSASEAPLKPGARIFSFDGRD
VLRHPTWPQRSVWHGSDPNGRRLTES
YCETWRTEAPSATGQASSLLGGRLLGQ
SAASCHHAYIVLCIENSFMTASR

Figure 41

MHSHRDFQPVLHLVALNSPLSGGMRG
IRGADFQCFQQARAVGLAGTFRAFLSS
RLQDLYSIVRRADRAAVPIVNLRDELLF
PSWEALFSPSEGPLKPGARIFSFDGRDV
LRHPTWPQRSVWHGSDPNGRRLTESY
CETWRTEAPSATGQASSLLGGRLLGQS
AASCHHAYIVLCIENSFMTASR

Figure 42

A
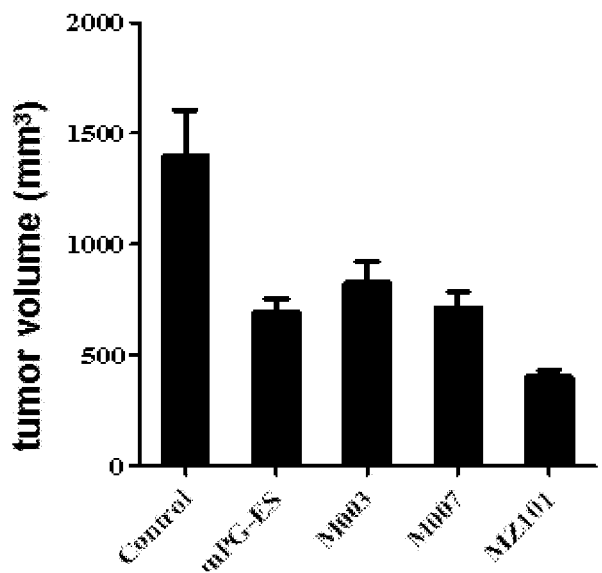
B
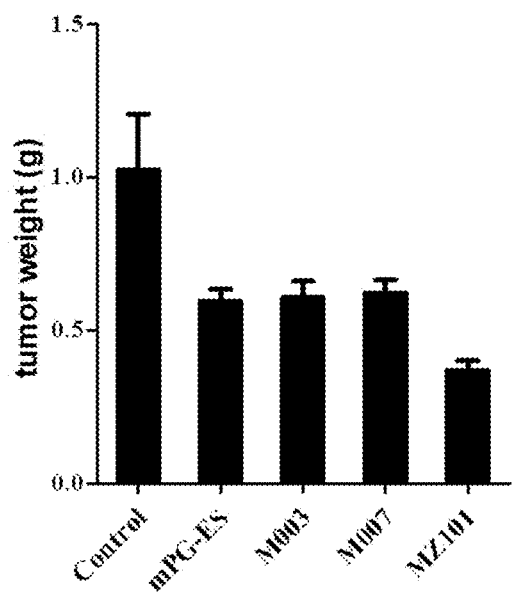
Figure 48

SEQUENCE LISTING

```
<160> NUMBER OF SEQ ID NOS: 33

<210> SEQ ID NO 1
<211> LENGTH: 183
<212> TYPE: PRT
<213> ORGANISM: Homo sapiens

<400> SEQUENCE: 1

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 2
<211> LENGTH: 184
<212> TYPE: PRT
<213> ORGANISM: Homo sapiens

<400> SEQUENCE: 2

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
```

```
                    50                  55                  60
Ala Asp Arg Ala Ala Val Pro Ile Val Asn Leu Lys Asp Glu Leu Leu
 65                  70                  75                  80

Phe Pro Ser Trp Glu Ala Leu Phe Ser Gly Ser Glu Gly Pro Leu Lys
                     85                  90                  95

Pro Gly Ala Arg Ile Phe Ser Phe Asp Gly Lys Asp Val Leu Arg His
                100                 105                 110

Pro Thr Trp Pro Gln Lys Ser Val Trp His Gly Ser Asp Pro Asn Gly
                115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
                180
```

<210> SEQ ID NO 3
<211> LENGTH: 180
<212> TYPE: PRT
<213> ORGANISM: Homo sapiens

<400> SEQUENCE: 3

```
Met Asp Phe Gln Pro Val Leu His Leu Val Ala Leu Asn Ser Pro Leu
  1               5                  10                  15

Ser Gly Gly Met Arg Gly Ile Arg Gly Ala Asp Phe Gln Cys Phe Gln
                 20                  25                  30

Gln Ala Arg Ala Val Gly Leu Ala Gly Thr Phe Arg Ala Phe Leu Ser
             35                  40                  45

Ser Arg Leu Gln Asp Leu Tyr Ser Ile Val Arg Arg Ala Asp Arg Ala
         50                  55                  60

Ala Val Pro Ile Val Asn Leu Lys Asp Glu Leu Leu Phe Pro Ser Trp
 65                  70                  75                  80

Glu Ala Leu Phe Ser Gly Ser Glu Gly Pro Leu Lys Pro Gly Ala Arg
                 85                  90                  95

Ile Phe Ser Phe Asp Gly Lys Asp Val Leu Arg His Pro Thr Trp Pro
                100                 105                 110

Gln Lys Ser Val Trp His Gly Ser Asp Pro Asn Gly Arg Arg Leu Thr
            115                 120                 125

Glu Ser Tyr Cys Glu Thr Trp Arg Thr Glu Ala Pro Ser Ala Thr Gly
        130                 135                 140

Gln Ala Ser Ser Leu Leu Gly Gly Arg Leu Leu Gly Gln Ser Ala Ala
145                 150                 155                 160

Ser Cys His His Ala Tyr Ile Val Leu Cys Ile Glu Asn Ser Phe Met
                165                 170                 175

Thr Ala Ser Lys
            180
```

<210> SEQ ID NO 4
<211> LENGTH: 192
<212> TYPE: PRT
<213> ORGANISM: Homo sapiens

<400> SEQUENCE: 4

Met Gly Gly Ser His His His His His His Ser His Arg Asp Phe Gln

```
            1               5                  10                 15
         Pro Val Leu His Leu Val Ala Leu Asn Ser Pro Leu Ser Gly Gly Met
                         20                  25                 30

Arg Gly Ile Arg Gly Ala Asp Phe Gln Cys Phe Gln Gln Ala Arg Ala
                         35                  40                 45

Val Gly Leu Ala Gly Thr Phe Arg Ala Phe Leu Ser Ser Arg Leu Gln
                         50                  55                 60

Asp Leu Tyr Ser Ile Val Arg Arg Ala Asp Arg Ala Ala Val Pro Ile
         65                  70                  75                 80

Val Asn Leu Lys Asp Glu Leu Leu Phe Pro Ser Trp Glu Ala Leu Phe
                         85                  90                 95

Ser Gly Ser Glu Gly Pro Leu Lys Pro Gly Ala Arg Ile Phe Ser Phe
                        100                 105                110

Asp Gly Lys Asp Val Leu Arg His Pro Thr Trp Pro Gln Lys Ser Val
                        115                 120                125

Trp His Gly Ser Asp Pro Asn Gly Arg Arg Leu Thr Glu Ser Tyr Cys
                        130                 135                140

Glu Thr Trp Arg Thr Glu Ala Pro Ser Ala Thr Gly Gln Ala Ser Ser
         145                 150                 155                160

Leu Leu Gly Gly Arg Leu Leu Gly Gln Ser Ala Ala Ser Cys His His
                        165                 170                175

Ala Tyr Ile Val Leu Cys Ile Glu Asn Ser Phe Met Thr Ala Ser Lys
                        180                 185                190

<210> SEQ ID NO 5
<211> LENGTH: 184
<212> TYPE: PRT
<213> ORGANISM: Homo sapiens

<400> SEQUENCE: 5

Met His Ser His Arg Asp Phe Gln Pro Val Leu His Leu Val Ala Leu
1               5                  10                 15

Asn Ser Pro Leu Ser Gly Gly Met Arg Gly Ile Arg Gly Ala Asp Phe
                20                  25                 30

Gln Cys Phe Gln Gln Ala Arg Ala Val Gly Leu Ala Gly Thr Phe Arg
                35                  40                 45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                 80

Phe Pro Ser Trp Glu Ala Leu Phe Ser Gly Ser Glu Gly Pro Leu Arg
                85                  90                 95

Pro Gly Ala Arg Ile Phe Ser Phe Asp Gly Lys Asp Val Leu Arg His
                100                 105                110

Pro Thr Trp Pro Gln Lys Ser Val Trp His Gly Ser Asp Pro Asn Gly
                115                 120                125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                160

Gln Ser Ala Ala Ser Cys His His Ala Tyr Ile Val Leu Cys Ile Glu
                165                 170                175

Asn Ser Phe Met Thr Ala Ser Lys
                180
```

<210> SEQ ID NO 6
<211> LENGTH: 184
<212> TYPE: PRT
<213> ORGANISM: Homo sapiens

<400> SEQUENCE: 6

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ala Ser Glu Gly Pro Leu Lys
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 7
<211> LENGTH: 184
<212> TYPE: PRT
<213> ORGANISM: Homo sapiens

<400> SEQUENCE: 7

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Ala Pro Leu Arg
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

```
Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 8
<211> LENGTH: 184
<212> TYPE: PRT
<213> ORGANISM: Homo sapiens

<400> SEQUENCE: 8

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
                20                  25                  30

Gln Cys Phe Gln Gln Ala Arg Ala Val Gly Leu Ala Gly Thr Phe Arg
            35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ala Ser Glu Ala Pro Leu Arg
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
            115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 9
<211> LENGTH: 184
<212> TYPE: PRT
<213> ORGANISM: Homo sapiens

<400> SEQUENCE: 9

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
                20                  25                  30

Gln Cys Phe Gln Gln Ala Arg Ala Val Gly Leu Ala Gly Thr Phe Arg
            35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Ala Pro Leu Lys
                85                  90                  95
```

-continued

```
Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 10
<211> LENGTH: 184
<212> TYPE: PRT
<213> ORGANISM: Homo sapiens

<400> SEQUENCE: 10

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ala Ser Lys Ala Pro Leu Gln
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 11
<211> LENGTH: 184
<212> TYPE: PRT
<213> ORGANISM: Homo sapiens

<400> SEQUENCE: 11

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45
```

```
Ala Phe Leu Ser Ser Arg Leu Gln Asp Leu Tyr Ser Ile Val Arg Arg
 50                  55                  60

Ala Asp Arg Ala Ala Val Pro Ile Val Asn Leu Lys Asp Glu Leu Leu
 65                  70                  75                  80

Phe Pro Ser Trp Glu Ala Leu Phe Ser Gly Ser Gln Gly Gln Leu Gln
                 85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
            115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180
```

<210> SEQ ID NO 12
<211> LENGTH: 192
<212> TYPE: PRT
<213> ORGANISM: Homo sapiens

<400> SEQUENCE: 12

```
Met Gly Gly Ser His His His His Ser His Arg Asp Phe Gln
  1               5                  10                  15

Pro Val Leu His Leu Val Ala Leu Asn Ser Pro Leu Ser Gly Gly Met
                 20                  25                  30

Arg Gly Ile Arg Gly Ala Asp Phe Gln Cys Phe Gln Gln Ala Arg Ala
             35                  40                  45

Val Gly Leu Ala Gly Thr Phe Arg Ala Phe Leu Ser Ser Arg Leu Gln
 50                  55                  60

Asp Leu Tyr Ser Ile Val Arg Arg Ala Asp Arg Ala Ala Val Pro Ile
 65                  70                  75                  80

Val Asn Leu Lys Asp Glu Leu Leu Phe Pro Ser Trp Glu Ala Leu Phe
                 85                  90                  95

Ser Gly Ser Glu Gly Pro Leu Arg Pro Gly Ala Arg Ile Phe Ser Phe
            100                 105                 110

Asp Gly Lys Asp Val Leu Arg His Pro Thr Trp Pro Gln Lys Ser Val
            115                 120                 125

Trp His Gly Ser Asp Pro Asn Gly Arg Arg Leu Thr Glu Ser Tyr Cys
130                 135                 140

Glu Thr Trp Arg Thr Glu Ala Pro Ser Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
            180                 185                 190
```

<210> SEQ ID NO 13
<211> LENGTH: 192
<212> TYPE: PRT
<213> ORGANISM: Homo sapiens

<400> SEQUENCE: 13

Met Gly Gly Ser His His His His His Ser His Arg Asp Phe Gln
1               5                   10                  15

Pro Val Leu His Leu Val Ala Leu Asn Ser Pro Leu Ser Gly Gly Met
                20                  25                  30

Arg Gly Ile Arg Gly Ala Asp Phe Gln Cys Phe Gln Gln Ala Arg Ala
            35                  40                  45

Val Gly Leu Ala Gly Thr Phe Arg Ala Phe Leu Ser Ser Arg Leu Gln
50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Ala Ser Glu Gly Pro Leu Lys Pro Gly Ala Arg Ile Phe Ser Phe
            100                 105                 110

Asp Gly Lys Asp Val Leu Arg His Pro Thr Trp Pro Gln Lys Ser Val
            115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
            180                 185                 190

<210> SEQ ID NO 14
<211> LENGTH: 192
<212> TYPE: PRT
<213> ORGANISM: Homo sapiens

<400> SEQUENCE: 14

Met Gly Gly Ser His His His His His Ser His Arg Asp Phe Gln
1               5                   10                  15

Pro Val Leu His Leu Val Ala Leu Asn Ser Pro Leu Ser Gly Gly Met
                20                  25                  30

Arg Gly Ile Arg Gly Ala Asp Phe Gln Cys Phe Gln Gln Ala Arg Ala
            35                  40                  45

Val Gly Leu Ala Gly Thr Phe Arg Ala Phe Leu Ser Ser Arg Leu Gln
50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Ser Gln Gly Gln Leu Gln Pro Gly Ala Arg Ile Phe Ser Phe
            100                 105                 110

Asp Gly Lys Asp Val Leu Arg His Pro Thr Trp Pro Gln Lys Ser Val
            115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
            180                 185                 190

<210> SEQ ID NO 15
<211> LENGTH: 184
<212> TYPE: PRT
<213> ORGANISM: Homo sapiens

<400> SEQUENCE: 15

Met His Ser His Met Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 16
<211> LENGTH: 184
<212> TYPE: PRT
<213> ORGANISM: Homo sapiens

<400> SEQUENCE: 16

Met His Ser His Gln Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
130                 135                 140

```
Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
            165                 170                 175

Asn Ser Phe Met Thr Ala Ser Lys
            180

<210> SEQ ID NO 17
<211> LENGTH: 184
<212> TYPE: PRT
<213> ORGANISM: Homo sapiens

<400> SEQUENCE: 17

Met His Ser His Gln Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Gln Gly Gln Leu Gln
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
            165                 170                 175

Asn Ser Phe Met Thr Ala Ser Lys
            180

<210> SEQ ID NO 18
<211> LENGTH: 181
<212> TYPE: PRT
<213> ORGANISM: Homo sapiens

<400> SEQUENCE: 18

Met Asp Phe Gln Pro Val Leu His Leu Val Ala Leu Asn Ser Pro Leu
1               5                   10                  15

Ser Gly Gly Met Arg Gly Ile Arg Gly Ala Asp Phe Gln Cys Phe Gln
            20                  25                  30

Gln Ala Arg Ala Val Gly Leu Ala Gly Thr Phe Arg Ala Phe Leu Ser
        35                  40                  45

Ser Arg Leu Gln Asp Leu Tyr Ser Ile Val Arg Arg Ala Asp Arg Ala
50                  55                  60

Ala Val Pro Ile Val Asn Leu Lys Asp Glu Leu Leu Phe Pro Ser Trp
65                  70                  75                  80

Glu Ala Leu Phe Ser Gly Ser Glu Gly Pro Leu Lys Ser Pro Gly Ala
                85                  90                  95
```

Arg Ile Phe Ser Phe Asp Gly Lys Asp Val Leu Arg His Pro Thr Trp
            100                 105                 110

Pro Gln Lys Ser Val Trp His Gly Ser Asp Pro Asn Gly Arg Arg Leu
            115                 120                 125

Thr Glu Ser Tyr Cys Glu Thr Trp Arg Thr Glu Ala Pro Ser Ala Thr
        130                 135                 140

Gly Gln Ala Ser Ser Leu Leu Gly Gly Arg Leu Leu Gly Gln Ser Ala
145                 150                 155                 160

Ala Ser Cys His His Ala Tyr Ile Val Leu Cys Ile Glu Asn Ser Phe
                165                 170                 175

Met Thr Ala Ser Lys
            180

<210> SEQ ID NO 19
<211> LENGTH: 181
<212> TYPE: PRT
<213> ORGANISM: Homo sapiens

<400> SEQUENCE: 19

Met Asp Phe Gln Pro Val Leu His Leu Val Ala Leu Asn Ser Pro Leu
1               5                   10                  15

Ser Gly Gly Met Arg Gly Ile Arg Gly Ala Asp Phe Gln Cys Phe Gln
            20                  25                  30

Gln Ala Arg Ala Val Gly Leu Ala Gly Thr Phe Arg Ala Phe Leu Ser
        35                  40                  45

Ser Arg Leu Gln Asp Leu Tyr Ser Ile Val Arg Arg Ala Asp Arg Ala
50                  55                  60

Ala Val Pro Ile Val Asn Leu Lys Asp Glu Leu Leu Phe Pro Ser Trp
65                  70                  75                  80

Glu Ala Leu Phe Ser Gly Ser Glu Gly Pro Leu Lys Thr Pro Gly Ala
                85                  90                  95

Arg Ile Phe Ser Phe Asp Gly Lys Asp Val Leu Arg His Pro Thr Trp
            100                 105                 110

Pro Gln Lys Ser Val Trp His Gly Ser Asp Pro Asn Gly Arg Arg Leu
            115                 120                 125

Thr Glu Ser Tyr Cys Glu Thr Trp Arg Thr Glu Ala Pro Ser Ala Thr
        130                 135                 140

Gly Gln Ala Ser Ser Leu Leu Gly Gly Arg Leu Leu Gly Gln Ser Ala
145                 150                 155                 160

Ala Ser Cys His His Ala Tyr Ile Val Leu Cys Ile Glu Asn Ser Phe
                165                 170                 175

Met Thr Ala Ser Lys
            180

<210> SEQ ID NO 20
<211> LENGTH: 185
<212> TYPE: PRT
<213> ORGANISM: Homo sapiens

<400> SEQUENCE: 20

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

```
Ala Phe Leu Ser Ser Arg Leu Gln Asp Leu Tyr Ser Ile Val Arg Arg
        50                  55                  60

Ala Asp Arg Ala Ala Val Pro Ile Val Asn Leu Lys Asp Glu Leu Leu
 65                  70                  75                  80

Phe Pro Ser Trp Glu Ala Leu Phe Ser Gly Ser Glu Gly Pro Leu Lys
                85                  90                  95

Ser Pro Gly Ala Arg Ile Phe Ser Phe Asp Gly Lys Asp Val Leu Arg
               100                 105                 110

His Pro Thr Trp Pro Gln Lys Ser Val Trp His Gly Ser Asp Pro Asn
               115                 120                 125

Gly Arg Arg Leu Thr Glu Ser Tyr Cys Glu Thr Trp Arg Thr Glu Ala
           130                 135                 140

Pro Ser Ala Thr Gly Gln Ala Ser Ser Leu Leu Gly Gly Arg Leu Leu
145                 150                 155                 160

Gly Gln Ser Ala Ala Ser Cys His His Ala Tyr Ile Val Leu Cys Ile
               165                 170                 175

Glu Asn Ser Phe Met Thr Ala Ser Lys
               180                 185
```

```
<210> SEQ ID NO 21
<211> LENGTH: 185
<212> TYPE: PRT
<213> ORGANISM: Homo sapiens

<400> SEQUENCE: 21
```

```
Met His Ser His Arg Asp Phe Gln Pro Val Leu His Leu Val Ala Leu
 1               5                  10                  15

Asn Ser Pro Leu Ser Gly Gly Met Arg Gly Ile Arg Gly Ala Asp Phe
                20                  25                  30

Gln Cys Phe Gln Gln Ala Arg Ala Val Gly Leu Ala Gly Thr Phe Arg
            35                  40                  45

Ala Phe Leu Ser Ser Arg Leu Gln Asp Leu Tyr Ser Ile Val Arg Arg
        50                  55                  60

Ala Asp Arg Ala Ala Val Pro Ile Val Asn Leu Lys Asp Glu Leu Leu
 65                  70                  75                  80

Phe Pro Ser Trp Glu Ala Leu Phe Ser Gly Ser Glu Gly Pro Leu Lys
                85                  90                  95

Thr Pro Gly Ala Arg Ile Phe Ser Phe Asp Gly Lys Asp Val Leu Arg
               100                 105                 110

His Pro Thr Trp Pro Gln Lys Ser Val Trp His Gly Ser Asp Pro Asn
               115                 120                 125

Gly Arg Arg Leu Thr Glu Ser Tyr Cys Glu Thr Trp Arg Thr Glu Ala
           130                 135                 140

Pro Ser Ala Thr Gly Gln Ala Ser Ser Leu Leu Gly Gly Arg Leu Leu
145                 150                 155                 160

Gly Gln Ser Ala Ala Ser Cys His His Ala Tyr Ile Val Leu Cys Ile
               165                 170                 175

Glu Asn Ser Phe Met Thr Ala Ser Lys
               180                 185
```

```
<210> SEQ ID NO 22
<211> LENGTH: 180
<212> TYPE: PRT
<213> ORGANISM: Homo sapiens

<400> SEQUENCE: 22
```

```
Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
            115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met
            180

<210> SEQ ID NO 23
<211> LENGTH: 182
<212> TYPE: PRT
<213> ORGANISM: Homo sapiens

<400> SEQUENCE: 23

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ser Glu Pro Leu Gln Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
            115                 120                 125

Leu Thr Glu Ser Tyr Cys Glu Thr Trp Arg Thr Glu Ala Pro Ser Ala
130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn Ser
                165                 170                 175

Phe Met Thr Ala Ser Lys
            180
```

<210> SEQ ID NO 24
<211> LENGTH: 183
<212> TYPE: PRT
<213> ORGANISM: Homo sapiens

<400> SEQUENCE: 24

Met His Ser His Gln Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 25
<211> LENGTH: 182
<212> TYPE: PRT
<213> ORGANISM: Homo sapiens

<400> SEQUENCE: 25

Met His Ser His Gln Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ser Glu Pro Leu Lys Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
        115                 120                 125

Leu Thr Glu Ser Tyr Cys Glu Thr Trp Arg Thr Glu Ala Pro Ser Ala

```
                130               135               140
Thr Gly Gln Ala Ser Ser Leu Leu Gly Gly Arg Leu Gly Gln Ser
145                 150               155               160

Ala Ala Ser Cys His His Ala Tyr Ile Val Leu Cys Ile Glu Asn Ser
                165               170               175

Phe Met Thr Ala Ser Lys
            180
```

<210> SEQ ID NO 26
<211> LENGTH: 183
<212> TYPE: PRT
<213> ORGANISM: Homo sapiens

<400> SEQUENCE: 26

```
Met His Ser His Gln Asp Phe Gln Pro Val Leu His Leu Val Ala Leu
1               5                   10                  15

Asn Ser Pro Leu Ser Gly Gly Met Arg Gly Ile Arg Gly Ala Asp Phe
                20                  25                  30

Gln Cys Phe Gln Gln Ala Arg Ala Val Gly Leu Ala Gly Thr Phe Arg
            35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ser Glu Gly Pro Leu Gln Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180
```

<210> SEQ ID NO 27
<211> LENGTH: 183
<212> TYPE: PRT
<213> ORGANISM: Homo sapiens

<400> SEQUENCE: 27

```
Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
                20                  25                  30

Gln Cys Phe Gln Gln Ala Arg Ala Val Gly Leu Ala Gly Thr Phe Arg
            35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Ser Glu Gly Pro Leu Lys Pro
```

```
                    85                  90                  95

Gly Ala Arg Ile Phe Ser Phe Asp Gly Arg Asp Val Leu Arg His Pro
                100                 105                 110

Thr Trp Pro Gln Arg Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
        130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Arg
                180

<210> SEQ ID NO 28
<211> LENGTH: 184
<212> TYPE: PRT
<213> ORGANISM: Homo sapiens

<400> SEQUENCE: 28

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Arg Asp Glu Leu Leu
65                  70                  75                  80

Phe Pro Ser Trp Glu Ala Leu Phe Ser Gly Ser Gln Gly Gln Leu Gln
                85                  90                  95

Pro Gly Ala Arg Ile Phe Ser Phe Asp Gly Arg Asp Val Leu Arg His
                100                 105                 110

Pro Thr Trp Pro Gln Lys Ser Val Trp His Gly Ser Asp Pro Asn Gly
            115                 120                 125

Arg Arg Leu Thr Glu Ser Tyr Cys Glu Thr Trp Arg Thr Glu Ala Pro
        130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Arg
                180

<210> SEQ ID NO 29
<211> LENGTH: 185
<212> TYPE: PRT
<213> ORGANISM: Homo sapiens

<400> SEQUENCE: 29

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
```

```
                35                  40                  45
Ala Phe Leu Ser Ser Arg Leu Gln Asp Leu Tyr Ser Ile Val Arg Arg
 50                  55                  60

Ala Asp Arg Ala Ala Val Pro Ile Val Asn Leu Lys Asp Glu Leu Leu
 65                  70                  75                  80

Phe Pro Ser Trp Glu Ala Leu Phe Ser Gly Glu Ser Gly Ala Gly Arg
                 85                  90                  95

Thr Pro Gly Ala Arg Ile Phe Ser Phe Asp Gly Lys Asp Val Leu Arg
                100                 105                 110

His Pro Thr Trp Pro Gln Lys Ser Val Trp His Gly Ser Asp Pro Asn
            115                 120                 125

Gly Arg Arg Leu Thr Glu Ser Tyr Cys Glu Thr Trp Arg Thr Glu Ala
130                 135                 140

Pro Ser Ala Thr Gly Gln Ala Ser Ser Leu Leu Gly Gly Arg Leu Leu
145                 150                 155                 160

Gly Gln Ser Ala Ala Ser Cys His His Ala Tyr Ile Val Leu Cys Ile
                165                 170                 175

Glu Asn Ser Phe Met Thr Ala Ser Lys
            180                 185

<210> SEQ ID NO 30
<211> LENGTH: 183
<212> TYPE: PRT
<213> ORGANISM: Homo sapiens

<400> SEQUENCE: 30

Met His Ser His Arg Asp Phe Gln Pro Val Leu His Leu Val Ala Leu
  1               5                  10                  15

Asn Ser Pro Leu Ser Gly Gly Met Arg Gly Ile Arg Gly Ala Asp Phe
                 20                  25                  30

Gln Cys Phe Gln Gln Ala Arg Ala Val Gly Leu Ala Gly Thr Phe Arg
             35                  40                  45

Ala Phe Leu Ser Ser Arg Leu Gln Asp Leu Tyr Ser Ile Val Arg Arg
 50                  55                  60

Ala Asp Arg Ala Ala Val Pro Ile Val Asn Leu Arg Asp Glu Leu Leu
 65                  70                  75                  80

Phe Pro Ser Trp Glu Ala Leu Phe Ser Ser Glu Gly Pro Leu Lys Pro
                 85                  90                  95

Gly Ala Arg Ile Phe Ser Phe Asp Gly Arg Asp Val Leu Arg His Pro
                100                 105                 110

Thr Trp Pro Gln Arg Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
130                 135                 140

Ala Thr Gly Gln Ala Ser Ser Leu Leu Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Arg
            180

<210> SEQ ID NO 31
<211> LENGTH: 184
<212> TYPE: PRT
<213> ORGANISM: Homo sapiens
```

```
<400> SEQUENCE: 31

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Arg Asp Glu Leu Leu
65                  70                  75                  80

Phe Pro Ser Trp Glu Ala Leu Phe Ser Ala Ser Glu Gly Pro Leu Lys
                85                  90                  95

Pro Gly Ala Arg Ile Phe Ser Phe Asp Gly Arg Asp Val Leu Arg His
            100                 105                 110

Pro Thr Trp Pro Gln Arg Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Arg
            180

<210> SEQ ID NO 32
<211> LENGTH: 184
<212> TYPE: PRT
<213> ORGANISM: Homo sapiens

<400> SEQUENCE: 32

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Arg Asp Glu Leu Leu
65                  70                  75                  80

Phe Pro Ser Trp Glu Ala Leu Phe Ser Ala Ser Glu Ala Pro Leu Lys
                85                  90                  95

Pro Gly Ala Arg Ile Phe Ser Phe Asp Gly Arg Asp Val Leu Arg His
            100                 105                 110

Pro Thr Trp Pro Gln Arg Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175
```

```
Asn Ser Phe Met Thr Ala Ser Arg
            180

<210> SEQ ID NO 33
<211> LENGTH: 184
<212> TYPE: PRT
<213> ORGANISM: Homo sapiens

<400> SEQUENCE: 33

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Arg Asp Glu Leu Leu
65                  70                  75                  80

Phe Pro Ser Trp Glu Ala Leu Phe Ser Pro Ser Glu Gly Pro Leu Lys
                85                  90                  95

Pro Gly Ala Arg Ile Phe Ser Phe Asp Gly Arg Asp Val Leu Arg His
            100                 105                 110

Pro Thr Trp Pro Gln Arg Ser Val Trp His Gly Ser Asp Pro Asn Gly
            115                 120                 125

Arg Arg Leu Thr Glu Ser Tyr Cys Glu Thr Trp Arg Thr Glu Ala Pro
130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Arg
            180
```

ENDOSTATIN MUTANTS WITH MUTATIONS AT ATP BINDING SITES

CROSS-REFERENCE OF THE RELATED APPLICATION

The present application is a 35 U.S.C. § 371 National Phase Entry Application of PCT/CN2012/081210, filed 10 Sep. 2012, designating the United States, which in turn claims priority to Chinese Patent Application No. 201110280441.8, filed on 9 Sep. 2011, both of which are incorporated herein by reference.

FIELD OF INVENTION

The present invention relates to a new anti-tumor therapeutic. In particular, this invention provides a mutant of endostatin, which has reduced ATPase activity and enhanced angiogenesis inhibiting activity. This invention also provides the use of the mutant in treating angiogenesis related diseases including tumor.

BACKGROUND OF INVENTION

In 1997, Professor Folkman from of Harvard University discovered the endogenous angiogenesis inhibitor—Endostatin (ES). Endostatin is a 20-kDa cleavage fragment of the C-terminus of collagen XVIII, which had inhibitory activities on the proliferation, migration of vascular endothelial cells, and the formation of blood vessels in vivo. The recombinant endostatin can inhibit the growth and metastasis of various types of tumors in mice, and can even cure the tumor without inducing drug resistance (Folkman J et al. Cell 1997; 88:277-285; Folkman J et al. Nature 1997; 390:404-407).

The mechanism underlying the inhibitory capacity of ES is that it suppresses the angiogenesis in tumor tissues and blocks the supply of nutrition and oxygen. In China, the recombinant human endostatin (Endu) expressed by E. coli has become an anti-tumor therapeutic and its anti-tumor effect has been widely tested in clinical trail mainly focused on non-small-cell lung carcinoma. Endu, a variant of ES, has additional amino acid sequence (MGGSHHHHH; SEQ ID NO:42) on N-terminal of ES, exhibiting more thermal dynamic stability and biological activity compared with wild type human ES expressed by yeast (Fu Y. et al. Biochemistry 2010; 49:6420-6429). Other report showed that the 27 amino acids on N-terminal of ES have the similar inhibitory activities on angiogenesis compared with the complete ES (Robert TjinThamSjin, et al., Cancer Res. 2005; 65(9):3656-63). Therefore, there are many researchers design medicaments based on the N-terminal 27 amino acids activities.

Furthermore, to prolong the half-life of ES in vivo, many molecular modifications and drug design have been made to ES, including single site or multiple sites PEG modifications and conjugation with antibody Fc fragment (Tong-Young Lee, et al., Clin Cancer Res 2008; 14(5):1487-1493). Multiple sites PEG modifications of ES are usually implemented on the amino of lysine side chain. Although this may prolong the half-life of ES, but its biological activities are apparently reduced (Guoying Mou, dissertation of Shandong University, CNKI, 2005). Compared with this modification technique, single site PEG modification on the N-terminal can not only enhance the stability, but also the biological activities of ES (CN100475270C). The related product has entered into clinical trail.

Since the discovery of ES, research projects from different laboratories focused on its tumor inhibitory activities have obtained different results. Professor Folkman's lab cured tumor in mice completely using ES (Folkman J et al., 1997, Nature, 390:404-407), but many other labs could not repeat this result (News Focus, 2002, Science, 295:2198-2199). Meanwhile, since the ES produced in the prokaryotic expressing system containing polar body that is very hard to refold, many researchers diverted to use yeast to produce resolvable ES, but this did not achieve ideal results. Subsequent studies observed that the yeast expressed ES was N-terminal truncated and the truncated forms were identified as N-1, N-3, and N-4. The integrity of N-terminal is very important to the stability and biological activity of ES, this explains the confusing results obtained from yeast expressed ES (Fu Y. et al. Biochemistry 2010; 49:6420-6429).

The primary biological function of ES is that is inhibits activities of endothelial cells, including inhibiting proliferation, migration and tube formation of endothelial cells and inducing apoptosis of endothelial cell, etc. The mechanism study of molecular function shows that nucleolin locating on the surface of plasma membrane is the functional receptor of ES and mediates the endocytosis of ES and its downstream signal pathway (Shi H B, et al., Blood, 2007, 110:2899-2906). Other report shows that nucleolin is also expressed on the plasma membrane of highly proliferative breast cancer cell line MDA-MB-435 and can mediate the endocytosis of its ligand protein in MDA-MB-435 (Sven Chridtian, et al., JBC, 2003, 163(4):871-878). In other studies, integrins, tropomyosin, glypican, laminin and matrix metalloproteinase 2 (MMP2) are all observed to be the potential receptors of ES (Sudhakar, A., et al., 2003, Proc. Natl. Acad. Sci. USA 100:4766-4771; Javaherian, K., et al., 2002, J. Biol. Chem., 277:45211-45218; Karumanchi, S., et al., 2001, Mol. Cell, 7:811-822; Lee, S. J., et al., 2002, FEBS Lett., 519:147-152; MacDonald, N. J., et al., 2001, J. Biol. Chem., 276:25190-25196; Kim, Y. M., et al., 2002, J. Biol. Chem., 277:27872-27879). Moreover, the treatment of nystatin dramatically increased the endocytosis and absorption of ES in endothelial cells, and therefore enhanced the biological activities of ES on inhibiting endothelial cells migration and animal tumor growth (Chen Y, et al., 2011, Blood, 117:6392-6403).

The classical method to detect the biological activities of ES is based on its activity of inhibiting the endothelial cells, including the inhibition of migration, proliferation and tube formation of endothelial cells and other experiments. Commonly used endothelial cells mainly comprise human vascular endothelial cells (HMEC) and human umbilical vein endothelial cells (HUVEC). However, these methods require high quality of cell culture and complicated techniques, are very subjective, and exhibit low accuracy and reproducibility (Li Y H, et al., 2011, Chin J Biological March, Vol. 24 No. 3:320-323). Therefore, to explore and develop new methods of evaluating the biological activities of ES and its mutants is of great importance in the ES drug discovery and quality control.

Adenosine triphosphate (ATP) is an essential energy supply to organisms, participating in multi physiological and biological reactions and plays an important role in maintaining normal organic activities. ATP can be produced in many cellular metabolic pathways: in the most classical pathway it is produced by adenosine triphosphate synthetase through oxidative phosphorylation in mitochondrial under normal conditions, or produced in chloroplast through photosynthesis in plant. The source for ATP synthesis is mainly glucose and fatty acid. Under normal physiological conditions, the molar concentration of ATP in cell and blood are 1-10 mM and 100 μM, respectively.

ATPase, also named adenosine triphosphotase, is an enzyme that catalyzes ATP to produce ADP and Pi and releasing energy. Under most conditions, the energy produced in this reaction can be transferred to another energy-required reaction and this process has been widely utilized in all known forms of lives. In addition, high-energy bond contained in the GTP can provide energy for protein synthesis, as well. Hsp90, myosin and other proteins all depend on ATP to perform biological activities, and thus all these proteins have ATPase activities. Although various kinds of ATPase are different in terms of sequence and tertiary structure, usually all these proteins have P-loop structure as the ATP binding motif (Andrea T. Deyrup, et al., 1998, JBC, 273(16):9450-9456). This P-loop structure exhibits the following typical sequences: GXXGXXK (SEQ ID NO:34) (Driscoll, W. J., et al., 1995 Proc. Natl. Acad. Sci. U.S.A., 92:12328-12332), (G/A)XXXXGK(T/S) (SEQ ID NO:35) (Walker, J., et al., 1982, EMBO J., 1:945-951), GXXXXGKS (SEQ ID NO:36) (Satishchandran, C., et al., 1992, Biochemistry, 31:11684-11688) and GXXGXGKS (SEQ ID NO:37) (Thomas, P. M., et al., 1995, Am. J. Hum. Genet., 59:510-518). Except for X, the remaining amino acid residues are relatively conserved. Generally, GTP also can bind to the ATP binding motif of these ATPases, and thus ATP and GTP can be alternative in many cases.

Cancer cells and highly proliferative cells including endothelial cells have abnormally strong metabolism and the metabolic pathways are greatly different from normal mature cells. On one hand, cancer cells and proliferative cells demand large amount of ATP; on the other hand, the efficacy of using glucose to produce ATP is very low in these cells. This is because most cancer cells and highly proliferative cells produce ATP through aerobic glycolysis (the Warburg effect). Although this pattern exhibits low efficacy to produce ATP, the numerous mediates synthesized in this process can be used as building blocks that are more better for cell proliferation (Matthew G, et al., 2009, Science, 324:1029-1033).

SUMMARY OF THE INVENTION

This invention discloses new activity of ES, namely ATPase activity, and discloses the new use of ES and ES drug design based on this new activity.

This invention is based on the discovery that ES exhibits strong ATPase activity. The in vitro experiments showed that the ATPase activity of ES is only slightly lower than that of Myosin (extract of pork heart), which is known to have naturally high ATPase activity, without significant differences in degenerating ATP from the endothelial cell lysate.

Based the ATPase activity of ES, this invention provides a new method of detecting and evaluating the biological activity of ES. This method makes it possible to determine the conformation and biological activity of recombinantly produced ES through detecting the extracellular ATPase activity of ES by means of biochemical assays. Compared with the present cytological detection method, this new approach based on enzyme activity is more sensitive and precise, easy to operate and reliable in reproducibility, and thus can be widely used to detect the biological activity and evaluate the quality of ES and its variants.

Therefore, this invention provides a method of detecting the biological activity of endostatin or a variant, mutant or PEG modified product thereof, including detecting the ATPase activity of the endostatin or a variant, mutant or PEG modified product thereof. For example, malachite green phosphate assay and ATP bioluminescence assay can be used to detect the ATPase activity of endostatin or a variant, mutant or PEG modified product thereof and thereby determining the conformation and biological activity of a recombinantly produced ES product.

It has been shown that ES can enter into the endothelial cell through nucleoclin-mediated endocytosis. In one example of this invention, to detect whether ES can execute ATPase activity intracellularly, the ATPase activity of ES was detected in endothelial cell lysate. The result shows that ES can execute ATPase activity in the endothelial cell lysate.

The inventors found that the $89^{th}$-$95^{th}$ amino acid residues Gly-Ser-Glu-Gly-Pro-Leu-Lys (SEQ ID NO:38) in the wild type ES sequence (SEQ ID NO.1) contains the conserved GXXGXXK (SEQ ID NO:34) sequence of classical ATP-binding motif (Driscoll, W. J., et al., 1995, Proc. Natl. Acad. Sci. U.S.A., 92:12328-12332). The three amino acids, two Gs and one K, are highly conserved in various species. ATPase activity of ES can be changed through point mutation in the ATP-binding motif. Although the crystal structure of ES has been known, there is no report on the crystal structure of the complex of ES with ATP or GTP. Using cocrystallization technique, it is possible in the future to identify other amino acid residues in the ES protein capable of interacting with ATP or GTP in addition to the classical binding motif sequence, and to change the ATPase activity of ES and its inhibitory effect on endothelial activity by deletion or substitution and other modifications of such amino acid residues.

Based on the known ES crystal structure, the inventors discovered that the ATP binding motif is close to the C-terminal of ES in the tertiary structure and the N-terminal is also very close to C-terminal in the tertiary structure. Therefore, in one example, the inventors compared ES variants with different N-terminal sequences and discovered that the ES variant with a deletion of four amino acids from the N-terminal (N-4) exhibited significantly higher ATPase activity than that of the full length ES. But it was previously reported that the N-4 exhibited significantly lower cytological activity and tumor inhibiting activity than ES (Fu Y. et al. Biochemistry 2010; 49:6420-6429).

It was also reported that murine ES (MM) could completely cure mouse tumor (Folkman J. et al. Nature 1997; 390:404-407). However, through amino acid sequence alignment analysis, we found that murine ES dose not contain the classical ATP binding motif of human ES (FIG. 1). Thus, we detected the ATPase activity of MM and discovered that it was significantly lower than that of human ES, which is only about one fifth of human ES. However, the tumor inhibitory effect of MM was higher than human ES.

Therefore, to further identify the relationship between the ATPase activity and the cytological activity of ES, we introduced point mutations to some amino acids of the ATP binding motif. We observed that these mutations not only changed the ATPase activity but also the inhibitory effect of ES on endothelial cell migration. Furthermore, some mutants of ES exhibited reduced ATPase activity, but the inhibitory effect on endothelial cell migration was significantly enhanced. Except for a few cases, the ATPase activity is negatively related to the cytological activity.

In some examples of this invention, mutants of ES comprising the sequence as shown in SEQ ID NO.6-11, 13, 14, 15-27 and 30-31 all exhibited reduced ATPase activity but equivalent or significantly higher inhibitory effect on endothelial cell migration. In view that ES is a vascular inhibiting protein and its essential function is to inhibit angiogenesis through inhibiting endothelial cell activity and thus can be used to treat angiogenesis related diseases (e.g., tumor, macular degeneration, obesity, and diabetes), we consider that these mutants of ES may process stronger activity to inhibit angiogenesis related diseases (e.g., tumor).

In addition, based on the correlation between anti-angiogenesis activity and the ATPase activity of ES, it might be possible to design ES mutants by further changing (reducing) the ATPase activity through molecular cloning techniques, so as to obtain ES mendicants which are more effective to inhibit tumor and angiogenesis related disease.

Therefore, this invention also provides a method of increasing the biological activity of endostatin, comprising reducing the ATPase activity of endostatin and its variants. In particular, genetic engineering approaches can be adopted to introduce mutations in the ATP binding motif GXXGXXK (SEQ ID NO:34) of endostatin or its variants to obtain an endostatin mutant with a reduced ATPase activity but an increased biological activity, for example, an increased inhibitory effect on endothelial cell migration and tumor growth.

This invention also provides endostatin mutants which are mutated in the ATP binding motif and exhibit enhanced anti-angiogenesis activity and decreased ATPase activity as compared to the wild type endostatin or its variants.

Preferably, the ATPase activity of the mutants is reduced at least about 30%, such as at least about 50%, at least about 70% or at least about 90%, as compared to the wild type endostatin or its variants. For example, the ATPase activity of the mutants is only about 60-70%, such as about 50-60%, 40-50%, 30-40%, 20-30%, 10-20% or no more than 10% or even lower, as compared to the wild type endostatin or its variants. In one embodiment, the mutant does not have ATPase activity.

In some embodiments, as compared with the corresponding wild type endostatin or its variant, the mutant comprises a mutation in the ATP combining motif. For example, the mutant comprises a mutation in the sequence corresponding to the Gly-Ser-Glu-Gly-Pro-Leu-Lys (SEQ ID NO:38) motif consisting of the 89$^{th}$-95$^{th}$ amino acid residues of SEQ ID NO.1, wherein the mutation is selected from the group consisting of one or several amino acid replacements, deletions or additions or a combination thereof, and the mutation results in a decrease or elimination of the ATPase activity in the mutant.

In some embodiments, the mutant comprises a partial or complete deletion of the sequence corresponding to the Gly-Ser-Glu-Gly-Pro-Leu-Lys (SEQ ID NO:38) motif consisting of the 89$^{th}$-95$^{th}$ amino acid residues of SEQ ID NO.1.

Preferably, the endostatin mutant of the invention comprises the following mutations: (a) Gly residue corresponding to the amino acid residue 89 of SEQ ID NO.1 is replaced with an uncharged or aromatic amino acid or deleted; or (b) Gly residue corresponding to the amino acid residue 92 of SEQ ID NO.1 is replaced with an uncharged amino acid or deleted; or (c) Lys residue corresponding to the amino acid residue 95 of SEQ ID NO.1 is replaced with a positive charged or uncharged amino acid or deleted; or (d) any combination of (a)-(c).

More preferably, the endostatin mutant of the invention comprises the following mutations: (a) Gly residue corresponding to the amino acid residue 89 of SEQ ID NO.1 is replaced with either Ala or Pro or deleted; or (b) Gly residue corresponding to the amino acid residue 92 of SEQ ID NO.1 is replaced with Ala or deleted; or (c) Lys residue corresponding to the amino acid residue 95 of SEQ ID NO.1 is replaced with either Arg or Gln or deleted; or (d) any combination of (a)-(c).

Of course, the above replacement can also be made with charged amino acids, with the prerequisite that it does not affect charge distribution and conformation of the mutant protein.

In a particular embodiment, the endostatin mutant of the invention comprises a sequence selected from the group consisting of SEQ ID NOs.6-11, 13, 14, 15-27 and 30-31. Preferably, the endostatin mutant of the invention comprises a sequence selected from the group consisting of SEQ ID NO.6, SEQ ID NO.10, SEQ ID NO.27 and SEQ ID NO.30.

Preferably, the endostatin mutant of the invention is a mutant of the human endostatin.

The invention also provides a pharmaceutical composition, which comprises the above mentioned endostatin mutant of the invention. In the pharmaceutical composition of the invention, the endostatin mutant may be covalently linked to the PEG molecule. The molecular weight of the PEG is such as 5-40KD, for example, 5-20KD, or 20-40KD. Preferably, the molecular weight of PEG is 20KD, for example the 20 kD monomethoxy Poly(ethylene glycol), or monomethoxy Poly(ethylene glycol)-aldehyde (mPEG-ALD). Preferably, the PEG molecule is covalently linked to the N-terminal α amino group of the endostatin.

The invention also provides a method of treating a tumor, comprising administering the aforementioned endostatin mutants or the pharmaceutical composition of the present invention to tumor patients.

The invention also relates to the use of the aforementioned endostatin mutants in preparation of a medicament for the treatment of a angiogenesis related disease. Preferably, the aforementioned angiogenesis related disease is tumor.

BRIEF DESCRIPTION OF THE DRAWINGS

FIG. 1 shows the sequence alignment of human ES (SEQ ID NO:1) and murine ES (SEQ ID NO:39).

FIG. 4 shows the ATPase activity of ES, ES variant and their mPEG modified products in endothelial cell lysate.
(A) ES and mPEG-ES can biodegrade ATP in endothelial cell lysate.
(B) ES, Endu and their mPEG modified products can biodegrade ATP in endothelial cell lysate.

FIG. 7 shows the comparison of the activity of ES mutants on biodegrading ATP in endothelial cell lysate.

FIG. 8 shows the comparison of the activity of ES mutants on inhibiting endothelial cell migration.

FIG. 9 shows the comparison of the ATPase activity and endothelial cell migration inhibiting activity of Endu mutants.

Figure 2:
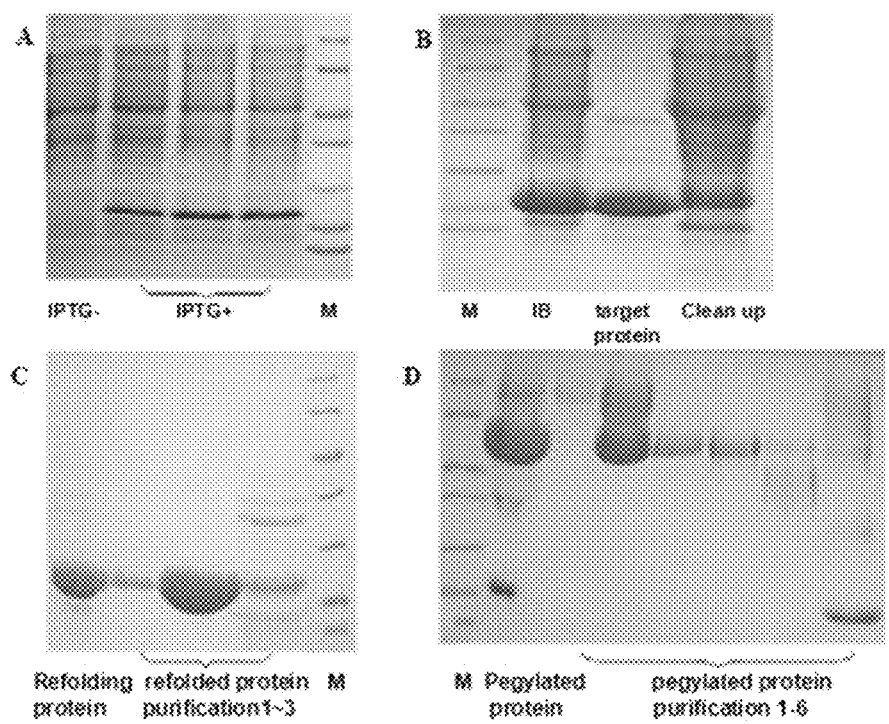
FIG. 2 shows the preparation of ES, ES mutant, ES variant and their mPEG modified products.
(A) Expression of engineering bacterium.
(B) Purification of inclusion body protein.
(C) Purification of refolded protein.
(D) Modified protein purification.

(A) The ATPase activity of Endu mutants.

(B) The activity of Endu mutants on inhibiting endothelial cell migration.

FIG. 10 shows the sequence of native human ES.

FIG. 11 depicts the sequence of recombinant human ES expressed in *E. coli*, in which the first amino acid M at the N-terminal can be randomly deleted during recombinant expression.

FIG. 12 depicts the sequence of recombinant human N-4 expressed in *E. coli*, in which the first amino acid M at the N-terminal and the last amino acid K can be randomly deleted during recombinant expression.

FIG. 13 depicts the sequence of recombinant human Endu expressed in *E. coli*, in which the first amino acid M at the N-terminal is randomly deleted during recombinant expression.

FIG. 14 depicts the sequence of recombinant human ES001 expressed in *E. coli*, in which the first amino acid M at the N-terminal can be randomly deleted during recombinant expression.

FIG. 15 depicts the sequence of recombinant human ES003 expressed in *E. coli*, in which the first amino acid M at the N-terminal can be randomly deleted during recombinant expression.

FIG. 16 depicts the sequence of recombinant humanES004 expressed in *E. coli*, in which the first amino acid M at the N-terminal can be randomly deleted during recombinant expression.

FIG. 17 depicts the sequence of recombinant human ES005 expressed in *E. coli*, in which the first amino acid M at the N-terminal can be randomly deleted during recombinant expression.

FIG. 18 depicts the sequence of recombinant human ES006 expressed in *E. coli*, in which the first amino acid M at the N-terminal can be randomly deleted during recombinant expression.

FIG. 19 depicts the sequence of recombinant human ES007 expressed in *E. coli*, in which the first amino acid M at the N-terminal can be randomly deleted during recombinant expression.

FIG. 20 depicts the sequence of recombinant human ES008 expressed in *E. coli*, in which the first amino acid M at the N-terminal can be randomly deleted during recombinant expression.

FIG. 21 depicts the sequence of recombinant human Endu001 expressed in *E. coli*, in which the first amino acid M at the N-terminal can be randomly deleted during recombinant expression.

FIG. 22 depicts the sequence of recombinant human Endu003 expressed in *E. coli*, in which the first amino acid M at the N-terminal can be randomly deleted during recombinant expression.

FIG. 23 depicts the sequence of recombinant human Endu008 expressed in *E. coli*, in which the first amino acid M at the N-terminal can be randomly deleted during recombinant expression.

FIG. 24 depicts the sequence of recombinant human ES010 expressed in *E. coli*, in which the first amino acid M at the N-terminal can be randomly deleted during recombinant expression.

FIG. 25 depicts the sequence of recombinant human ES011 expressed in *E. coli*, in which the first amino acid M at the N-terminal can be randomly deleted during recombinant expression.

FIG. 26 depicts the sequence of recombinant human ES012 expressed in *E. coli*, in which the first amino acid M at the N-terminal can be randomly deleted during recombinant expression.

FIG. 27 depicts the sequence of recombinant human S01 expressed in *E. coli*, in which the first amino acid M at the N-terminal can be randomly deleted during recombinant expression.

FIG. 28 depicts the sequence of recombinant human S02 expressed in *E. coli*, in which the first amino acid M at the N-terminal can be randomly deleted during recombinant expression.

FIG. 29 depicts the sequence of recombinant human S09 expressed in *E. coli*, in which the first amino acid M at the N-terminal can be randomly deleted during recombinant expression.

FIG. 30 depicts the sequence of recombinant human S10 expressed in *E. coli*, in which the first amino acid M at the N-terminal is randomly deleted during recombinant expression.

FIG. 31 depicts the sequence of recombinant human S12 expressed in *E. coli*, in which the first amino acid M at the N-terminal is randomly deleted during recombinant expression.

FIG. 32 depicts the sequence of recombinant human Z005 expressed in *E. coli*, in which the first amino acid M at the N-terminal is randomly deleted during recombinant expression.

FIG. 33 depicts the sequence of recombinant human Z006 expressed in *E. coli*, in which the first amino acid M at the N-terminal is randomly deleted during recombinant expression.

FIG. 34 depicts the sequence of recombinant human Z008 expressed in *E. coli*, in which the first amino acid M at the N-terminal is randomly deleted during recombinant expression.

FIG. 35 depicts the sequence of recombinant human Z009 expressed in *E. coli*, in which the first amino acid M at the N-terminal is randomly deleted during recombinant expression.

FIG. 36 depicts the sequence of recombinant human Z101 expressed in *E. coli*, in which the first amino acid M at the N-terminal is randomly deleted during recombinant expression.

FIG. 37 depicts the sequence of recombinant human Z103 expressed in *E. coli*, in which the first amino acid M at the N-terminal is randomly deleted during recombinant expression.

FIG. 38 depicts sequence of recombinant human Z104 expressed in *E. coli*, in which the first amino acid M at the N-terminal can be randomly deleted during recombinant expression.

FIG. 39 depicts the sequence of recombinant human ZN1 expressed in *E. coli*, in which the first amino acid M at the N-terminal is randomly deleted during recombinant expression.

FIG. 40 depicts the sequence of recombinant human ZN2 expressed in *E. coli*, in which the first amino acid M at the N-terminal is randomly deleted during recombinant expression.

FIG. 41 depicts the sequence of recombinant human ZN3 expressed in *E. coli*, in which the first amino acid M at the N-terminal is randomly deleted during recombinant expression.

FIG. 42 depicts the sequence of recombinant human ZN4 expressed in *E. coli*, in which the first amino acid M at the N-terminal is randomly deleted during recombinant expression.

Figure 43:
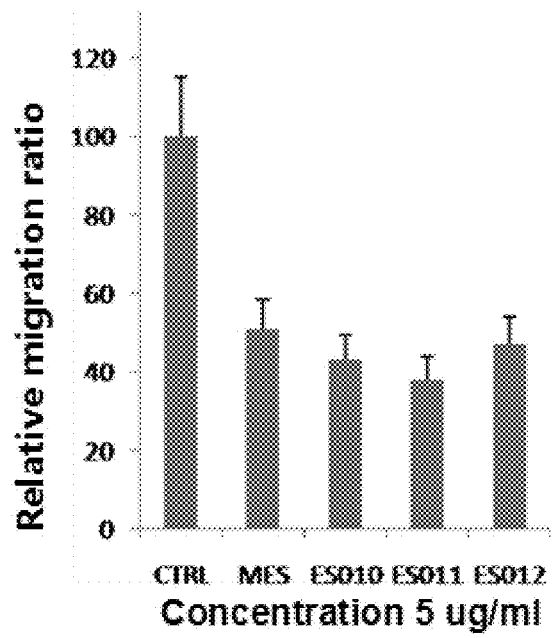

FIG. 43 shows the comparison of the endothelial cell migration inhibiting effect of ES mutants ES010, ES011, ES012.

Figure 44:
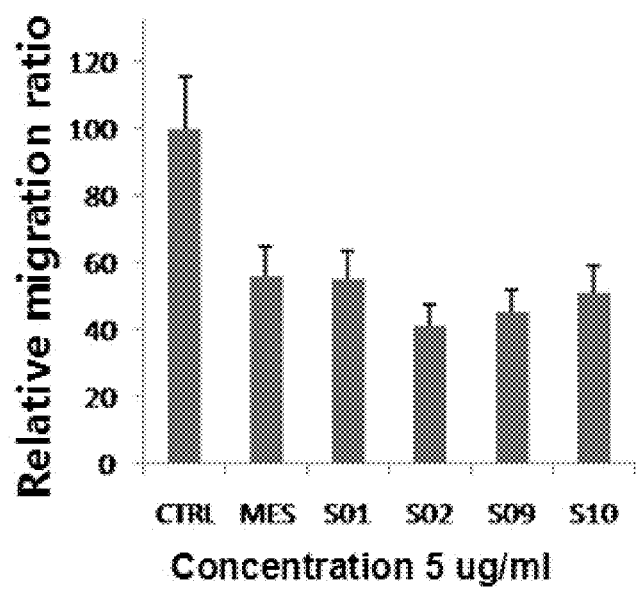

FIG. 44 shows the comparison of the endothelial cell migration inhibiting effect of ES mutants S01, S02, S09, S10.

Figure 45:
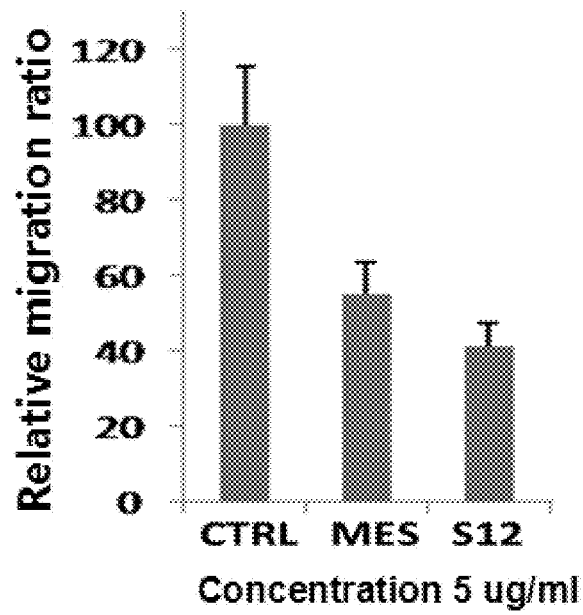

FIG. 45 shows the comparison of the endothelial cell migration inhibiting effect of ES mutants S12.

Figure 46:
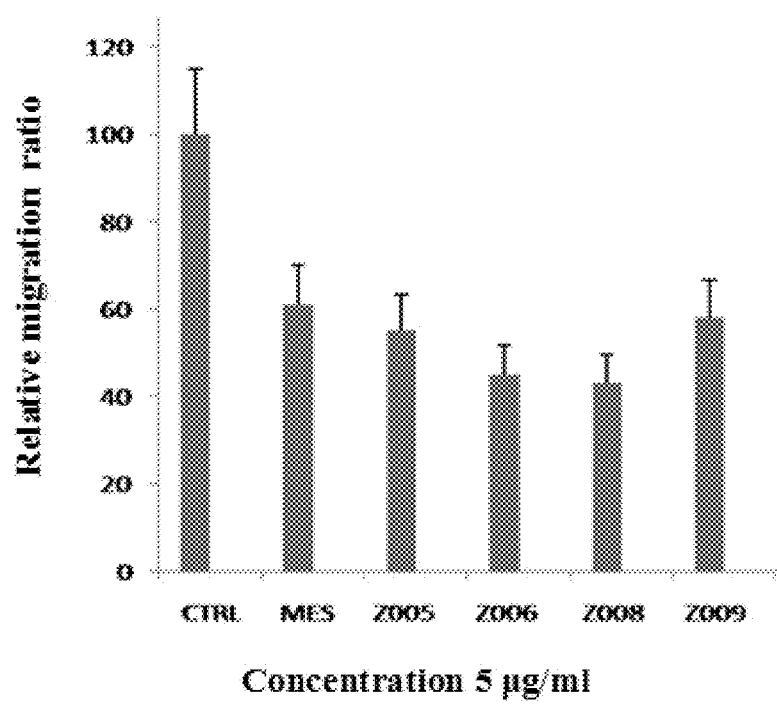

FIG. 46 shows the comparison of the endothelial cell migration inhibiting effect of ES mutants Z005, Z006, Z008, Z009.

Figure 47:
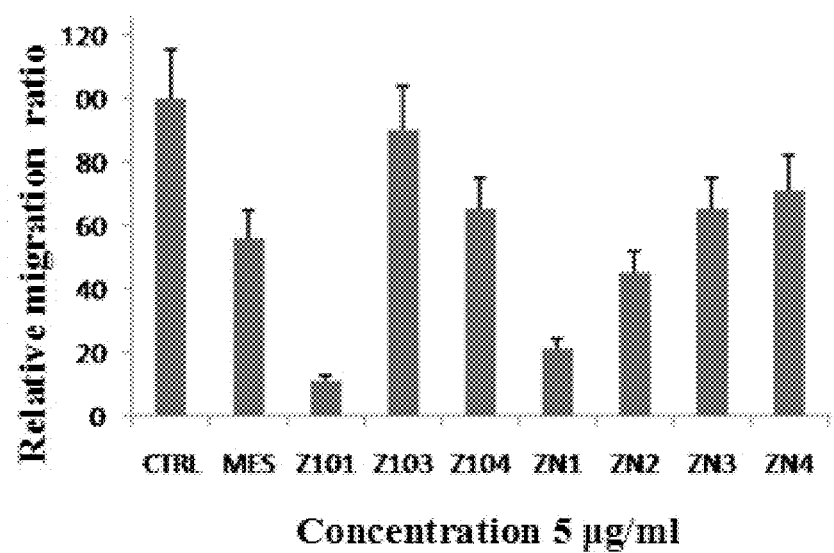

FIG. 47 shows the comparison of the endothelial cell migration inhibiting effect of ES mutants Z101, Z103, Z104, ZN1, ZN2, ZN3, ZN4.

FIG. 48 shows the inhibitory effect of ES mutants on non-small cell lung cancer A549 tumor growth at the animal level, (A) tumor volume, and (B) tumor weight.

DETAILED DESCRIPTION OF THE INVENTION

Unless otherwise indicated, the scientific and technical terms used in this description should have the meaning that a skilled person generally understands in this field. Normally, the nomenclature and techniques used in this description about cell and tissue culture, molecular biology, immunology, microbiology, genetics, and protein and nucleic acid chemistry are known and commonly used in this field.

Unless otherwise indicated, the methods and techniques used in this description normally are conducted according to commonly known and conventional methods of this field and described in this description or methods described in the cited references. For example, see Sambook J. and Russell D. Molecular Cloning: A Laboratory Manual, the third edition, Cold Spring Harbor Laboratory Press, Cold Spring Harbor, N.Y. (2000); Ausubel et al, Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al, Short Protocols in Protein Science, Wiley, John& Sons, Inc. (2003).

All the publications, patents and patent applications referenced in this description are incorporated by reference in their entirety.

ES, ES Variants, ES Mutants and their mPEG Modified Products

ES (Endostatin) refers to natural endostatin, for example, the human endostatin with the sequence of SEQ ID NO.1 (FIG. 10). ES variants refer to a molecule comprising an addition or a deletion of 1-15 amino acids at either N-terminal or C-terminal of a natural ES molecule. ES variant can be a naturally occurring variant, for example, when the human ES is recombinantly expressed in *E. coli*, the first amino acid M can be randomly deleted, producing an ES variant with the sequence of SEQ ID NO.2 (FIG. 11). For another example, when the ES is recombinantly expressed in yeast, due to random cutting of the N-terminal, an ES variant with a deletion of four amino acids from N-terminal can be produced, which variant has the sequence of SEQ ID NO.3 (FIG. 12). Further, the C-terminal K can also be randomly deleted. ES variant can also be a artificial variant. For example, to improve the expression and stability, Endu, an ES variant having the SEQ ID NO.4 sequence, has an addition of nine amino acids with the sequence of MGGSHHHHH (SEQ ID NO:42) at N-terminal of wild type ES (FIG. 13), and the first amino acid M can be randomly deleted during the recombinant expression. In this application, ES variants refer to a naturally occurring or artificial variant of ES, which has the same or similar activity of inhibiting angiogenesis and has the same or similar ATP binding motif and ATPase activity with the corresponding wild type ES.

In this application, ES mutant refer to a mutated protein obtained by modifying the ATP binding sites of a natural ES or ES variants, for example, by modifying the ATP binding motif by means of amino acid point mutation.

Except for Endu which was purchased from Medgenn, and the ES, ES variants, ES mutants used in this invention were provided by PROTGEN.

PEG modified ES, Endu, and N-4 are respectively named mPEG-ES, mPEG-Endu and mPEG-N-4. These products are ES, Endu, and N-4 respectively modified by 20 kD monomethoxy Poly(ethylene glycol)-aldehyde (mPEG-ALD), the coupling site for the activated mPEG-ALD aldehyde group is the N-terminal α amino group of ES, Endu, and N-4.

ATP Bioluminescence Assay Kit (Sigma-Aldrich)

This ATP assay is a well approved and widely used method, which has extreme sensitivity, and the principle is as follows. Firefly luciferase catalyzes the oxidation of luciferin to emit photons with the energy in ATP. Therefore, in the luminous reaction catalyzed by firefly luciferase, luminous intensity has well linear relationship with ATP concentration in the detection systems. By using bioluminescence analyzer (Berthold Technologies Centro LB 960) to detect luminous intensities in the reaction system, the ATP concentrations in reaction systems can be accurately calculated.

Malachite Green Phosphate Assay Kits (BioAssay Systems)

This is a well approved and widely used method to test ATPase activity. The principle is as follows. In acidic condition, the reaction between malachite green, molybdate and phosphoric acid can generate green substance, which can be detected in 600-660 nm wavelength range. The absorbance has well linear relationship with the phosphate concentration over a certain range. ADP and Pi are released during ATP hydrolysis catalyzed by ATPase. Therefore it is possible to calculate ATPase activity by the phosphate concentration detected by this kit. This method is convenient and expeditious, widely used to analyze the activities of phosphatase, lipase and nucleoside triphosphatase, and phosphate concentration as well as in high-throughput drug screening.

ATP-Binding Motif

These motifs refer to the classical primary sequence which can bind to ATP in proteins with ATPase activity. ATP-binding motif usually has a P-loop structure, which have some classical sequences, including GXXGXXK (SEQ ID NO:34), (G/A)XXXXGK(T/S) (SEQ ID NO:35), GXXXXGKS (SEQ ID NO:36) and GXXGXGKS (SEQ ID NO:37). Among these, amino acid residues which are not replaced by X are relatively conservative. Generally, these ATP-binding motifs can also bind to GTP.

ATP-Binding Site

These sites refer to the sites which can bind to ATP in proteins with ATPase activity, including classical ATP-binding motifs and other amino acid sites involved in ATP binding. These amino acid residues could be far from ATP-binding motifs on primary sequences, but they participate in the interaction between ES and ATP/GTP in tertiary structure. Alternatively, missing or replacement on these sites can indirectly disturb the interaction between ES and ATP/GTP by interfering protein conformation.

Based on the discovery of a new ES activity, i.e., ATPase activity, the invention provides a new method for evaluating the biological activity of ES. Compared with the current assay based on endothelial cell migration, this method is more convenient and accurate and proves to be well reproducible. This invention provides an important research approach for studying the action mechanism of ES, ES variants and ES mutants, as well as for drug development and quality control.

Therefore, this invention provides a method for detecting the bioactivities of ES, ES variant, ES mutant and PEG modified ES product. The method comprises detecting the ATPase activity of ES, ES variant, ES mutant and PEG modified ES as mentioned above. For example, it is possible to use malachite green phosphate assay kits or ATP bioluminescence assay kit to detect the ATPase activity of ES, ES variant, ES mutant and PEG modified ES, so as to determine the conformation and bioactivity of recombinant produced ES.

Meanwhile, compared with some known P-loop structure sequences in ATP-binding motifs, we found that in ES primary sequence, the amino acid residues from 89-95 having the sequence of Gly-Ser-Glu-Gly-Pro-Leu-Lys (SEQ ID NO:38) conform to the classical ATP-binding motif of GXXGXXK (SEQ ID NO:34), which is the structure basis for ES ATPase activity (FIG. 10).

Figure 3:
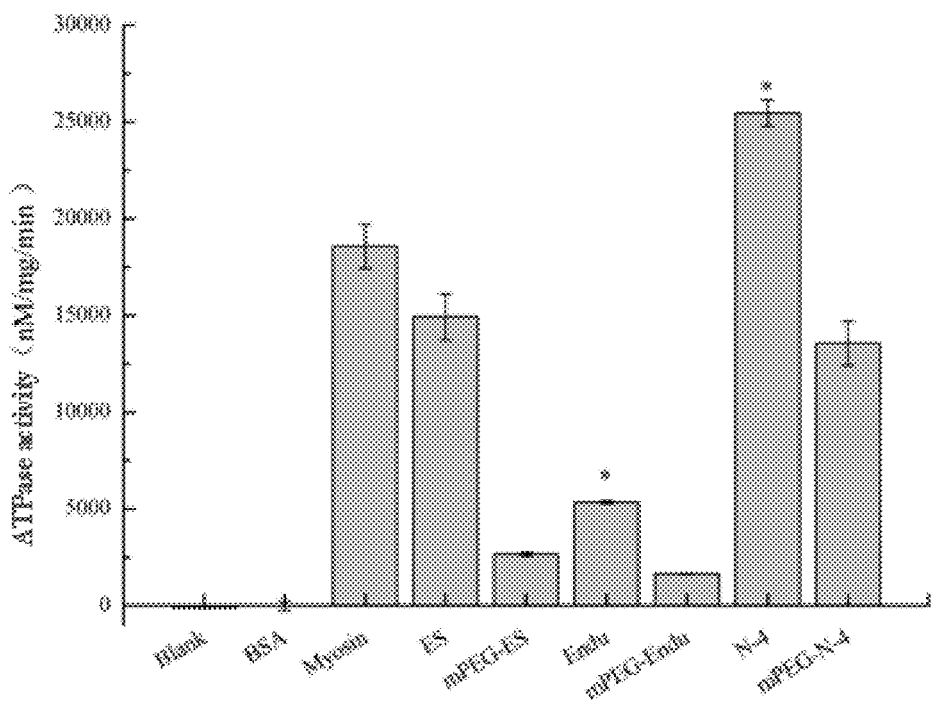
FIG. 3 shows the ATPase activity of ES, ES variant and their mPEG modified products.

Based on crystal structure of ES, we found that ES ATP-binding motif was close to N-terminal in tertiary structure, so the stereo specific blockade changes induced by N-terminal sequence alteration may influence the ATPase ability of ES. So in one example of this invention, we detected the ATPase activities of ES variant Endu (with 9 additional amino acid residues at N-terminal) and N-4 (with 4 amino acid deletion at N-terminal). The results showed that ES variants, Endu and N-4, had ATPase activities. ATPase activity of Endu was significantly reduced compared with ES, while ATPase activity of N-4 was significantly increased (FIG. 3). These results indicated that stereo specific blockade changes induced by different N-terminal integrity indeed have impact on the ATPase activity of ES. Therefore, apart from the classical ATP-binding motif GXXGXXK (SEQ ID NO:34), other ATP-interacting sites confirmed by cocrystallization analysis could be potential target sites for modifying the ATPase activity.

It has been reported that after single-point modification by mPEG at the N-terminal alpha-amino, the activities of ES and Endu to inhibit endothelial cell migration were significantly improved (CN 100475270C). So in one example of this invention, we detected the ATPase activities of mPEG-ES, mPEG-Endu, and mPEG-N-4, and found that the ATPase activities were significantly reduced (FIG. 3). So in this group of ES, ES variants and their mPEG modification products, the ATPase activities were negatively related to the activities of inhibiting endothelial cell migration, thus the higher ATPase activity, the lower activity of inhibiting endothelial cell migration. This result was confirmed by ES variant N-4: the ATPase activity of N-4 was higher than ES and Endu (FIG. 3), while other cellular activities were significantly reduced (Fu Y. et al. Biochemistry 2010; 49:6420-6429).

From the above data, we found that in ES, ES variants and their mPEG modification products, ATPase activities were negatively related to the activities of inhibiting endothelial cell migration. Based on this discovery, in order to obtain ES with higher activity of inhibiting endothelial cell migration, we introduced point mutations at ATP-binding sites in ES to reduce its ATPase activity.

Accordingly, this invention provides a method for improving the biological activity of ES, comprising reducing the ATPase activity of ES and ES variants. In particular, the ATP-binding motif GXXGXXK (SEQ ID NO:34) of ES and ES variants could be mutated by means of genetic engineering, and thereby obtaining an ES mutant with lower ATPase activity but improved biological activity, such as the activity of inhibiting endothelial cell migration and tumor.

In one example of this invention, the following mutations were introduced into ES ATP-binding sites:

| | |
|---|---|
| ES001—ES-K96R | (SEQ ID NO. 5) (FIG. 14) |
| ES003—ES-G90A | (SEQ ID NO. 6) (FIG. 15) |
| ES004—ES-G93A&K96R | (SEQ ID NO. 7) (FIG. 16) |
| ES005—ES-G90A&G93A&K96R | (SEQ ID NO. 8) (FIG. 17) |
| ES006—ES-G93A | (SEQ ID NO. 9) (FIG. 18) |
| ES007—ES-G90A&E92K&G93A&K96R | (SEQ ID NO. 10) (FIG. 19) |
| ES008—ES-E92Q&P94Q&K96Q | (SEQ ID NO. 11) (FIG. 20) |

Figure 6:
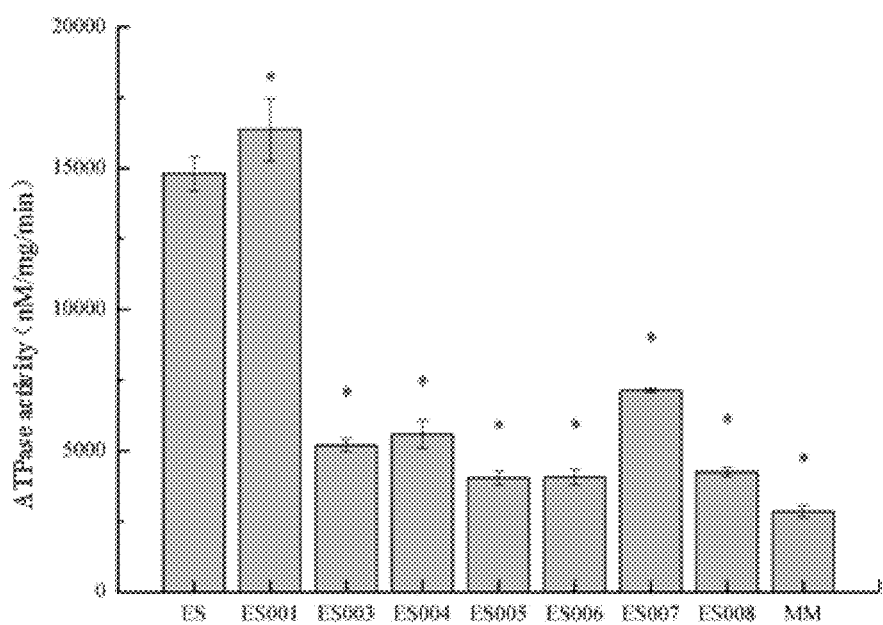
FIG. 6 shows the comparison of ATPase activity of ES mutants.

As detected by using biochemistry methods, the ATPase activities of the mutants were significantly increased as compared with ES, while the ATPase activities of mutants ES003, ES004, ES005, ES006, and ES007 were significantly reduced (FIG. 6). Although ES can be endocytosed by endothelial cells and degrade intracellular ATP, living cells can rapidly compensate the ATP consumption. So, instead of detecting the ATP concentration in living cells, current methods usually are designed to detect ATP degradation in whole cell lysate. In whole cell lysate, the ATPase activities of mutants ES003, ES006, ES007, and ES008 were still significantly lower than ES (FIG. 7A), but the ATPase activities of mutants ES001, ES004, and ES005 were equal to ES (FIG. 7B). This may be due to the P-loop structure changes induced by these mutations which may influence the interaction between the whole protein and ATP.

Subsequently, we continued to verify the activities of these ES mutants to inhibit endothelial cell migration. The results were basically in agreement with our expectation. Except for a very few mutants, the ATPase activity of most ES mutants were negatively related to the activity of inhibiting endothelial cell migration (FIG. 8).

In addition, in one example of this invention, the following mutations were introduced into an ES variant, Endu:

| | |
|---|---|
| Endu001—Endu-K104R | (SEQ ID NO. 12) (FIG. 21) |
| Endu003—Endu-G98A | (SEQ ID NO. 13) (FIG. 22) |
| Endu008—Endu-E100Q&P102Q&K104Q | (SEQ ID NO. 14) (FIG. 23) |

We found that when compared with ES, mutations in ATP-binding sites had similar impact on Endu in terms of the ATPase activities and inhibition of endothelial cell migration. Therefore, it is believed that the strategy of changing the ATPase activity and the inhibition of endothelial cells migration by introducing mutations in ATP-binding sites also applies to ES variants.

Therefore, this invention also provides an ES mutant with improved anti-angiogenesis activity. The mutant comprises a mutation at ATP-binding sites. Compared with the wild type ES or its variants, the mutant exibits reduced ATPase activity.

Preferably, the ATPase activity of the mutant is reduced at least about 30%, such as at least about 50%, at least about 70% or at least about 90%, as compared to the wild type endostatin or its variants. For example, the ATPase activity of the mutants is only about 60-70%, such as about 50-60%, 40-50%, 30-40%, 20-30%, 10-20% or no more than 10% or even lower, as compared to the wild type endostatin or its variants. In one example, the mutant had no ATPase activity.

In some embodiments, the mutant comprises a mutation in the ATP-binding motif as compared with the corresponding wild type endostatin or a variant thereof. For example, the mutant comprises a mutation in the sequence corresponding to the Gly-Ser-Glu-Gly-Pro-Leu-Lys (SEQ ID NO:38) motif consisting of amino acid residues 89-95 of SEQ ID NO.1, wherein said mutation is one or several amino acid replacement, deletion or addition, and said mutation results in a decrease or deletion of ATPase activity of said mutant.

In some embodiments, the mutant comprises a partial or complete deletion of the sequence corresponding to the Gly-Ser-Glu-Gly-Pro-Leu-Lys (SEQ ID NO:38) motif consisting of the 89$^{th}$-95$^{th}$ amino acid residues of SEQ ID NO.1.

Preferably, the ES mutant in the invention comprises the following mutations: (a) Gly residue corresponding to the amino acid residue 89 of SEQ ID NO.1 is replaced with an uncharged or aromatic amino acid or deleted; or (b) Gly residue corresponding to the amino acid residue 92 of SEQ ID NO.1 is replaced with an uncharged amino acid or deleted; or (c) Lys residue corresponding to the amino acid residue 95 of SEQ ID NO.1 is replaced with a positive charged or uncharged amino acid or deleted; or (d) any combination of (a)-(c).

More preferably, the ES mutant of the invention comprises the following mutations: (a) Gly residue corresponding to the amino acid residue 89 of SEQ ID NO.1 is replaced with either Ala or Pro or deleted; or (b) Gly residue corresponding to the amino acid residue 92 of SEQ ID NO.1 is replaced with Ala or deleted; or (c) Lys residue corresponding to the amino acid residue 95 of SEQ ID NO.1 is replaced with either Arg or Gln or deleted; or (d) any combination of (a)-(c).

In a particular embodiment, the ES mutant of the invention comprises a sequence selected from the group consisting of SEQ ID NOs.6-11, 13, 14, 15-27 and 30-31. Preferably, the ES mutant of the invention comprises a sequence selected from the group consisting of SEQ ID NO.6, SEQ ID NO.10, SEQ ID NO.27 and SEQ ID NO.30.

Preferably, the ES mutant of this invention is a mutant of the human ES.

This invention also provides a pharmaceutical composition comprising the mentioned above ES mutant. In the pharmaceutical composition of the invention, the ES mutant may be covalently linked to a PEG molecule. The molecular weight of the PEG is such as 5-40 kD, for example, 5-20 kD, or 20-40 kD. Preferably, the PEG has a molecular weight of 20 kD, for example, 20 kD mPEG or mPEG-ALD. Preferably, the PEG molecule is covalently linked to the N-terminal alpha amino group of the ES.

This invention also provides a method of treating a tumor, comprising administering the aforementioned endostatin mutant or pharmaceutical composition of the present invention to a patient having a tumor.

This invention also relates to the use of the aforementioned endostatin mutants in preparation of a medicament for the treatment of an angiogenesis related disease. Preferably, the aforementioned angiogenesis related disease is tumor.

This invention will be further elucidated with the following non-exclusive examples, but it should be understood that this invention is not limited to these examples.

EXAMPLES

Example 1: Construction of ES Recombinant Strain

The gene of Endostatin was amplified from cDNA of lung cancer cell A549, and then was cloned into pET30a plasmid to obtain a recombinant plasmid. The 5'-primer for gene amplification was GGAATTCCATATGCACAGCCAC-CGCGACTTC (SEQ ID NO:40), and the 3'-primer was CCGCTCGAGTTACTTGGAGGCAGTCATGAAGCTG (SEQ ID NO:41). The restriction endonucleases were NdeI and XhoI respectively. The above recombinant plasmid was transformed into *E. coli* via conventional techniques in the art for further protein expression.

Example 2: Construction of the Strains Producing ES or Endu Mutants Containing a Mutated ATP Binding Site The ATP binding site of wild type human ES was modified by mutation. The detail mutation process, the primer pairs and the transformation process were the same as example 1. The mutants were listed as follows:

| | |
|---|---|
| ES001—ES-K96R | (SEQ ID NO. 5) (FIG. 14) |
| ES003—ES-G90A | (SEQ ID NO. 6) (FIG. 15) |
| ES004—ES-G93A&K96R | (SEQ ID NO. 7) (FIG. 16) |
| ES005—ES-G90A&G93A&K96R | (SEQ ID NO. 8) (FIG. 17) |
| ES006—ES-G93A | (SEQ ID NO. 9) (FIG. 18) |
| ES007—ES-G90A&E92K&G93A&K96R | (SEQ ID NO. 10) (FIG. 19) |
| ES008—ES-E92Q&P94Q&K96Q | (SEQ ID NO. 11) (FIG. 20) |

As controls, we also constructed the mutants containing a mutated ATP binding site, i.e. Endu001, Endu003 and Endu008, by using the same protocol as the above based on the sequence of wild type Endu.

Endu001—Endu-K104R (SEQ ID NO.12) (FIG. 21)
Endu003—Endu-G98A (SEQ ID NO.13) (FIG. 22)
Endu008—Endu-E100Q&P102Q&K104Q (SEQ ID NO.14) (FIG. 23)

Example 3: Preparation of Recombinant ES, ES Mutant and Endu Mutant

The preparation of mutant ES003 was taken as an example for illustrating the expression and preparation of recombinant ES, ES mutant and Endu mutant. Specifically, the strains for producing ES and its mutants were cultured in a shake flask containing LB medium over night, and then inoculated into a 5 L fermenter (Sartorius). IPTG was added at the appropriate time, and then the bacteria were harvested after about 4 hours (FIG. 2A). The bacteria were resuspended in a buffer solution and deeply broken by a high pressure homogenizer, and the broken bacteria were centrifuged to collect pellets. This process was repeated for three times. Then, DEAE column or Q column (GE Healthcare), and CM column or SP column (GE Healthcare) were used for the elution of proteins with a pH gradient of 4.0 to 10.0.

The renatured and un-renatured proteins were purified respectively, so as to obtain the renatured proteins with purity greater than 95% (FIG. 2B, C). The renatured proteins were concentrated and then dialyzed with PBS or NaAc-HAc. The modification of N-terminal of the renatured proteins was performed by using monomethoxy Poly(ethylene glycol)-aldehyde (mPEG-ALD, 20 kDa, Beijing JenKem Technology Co., Ltd.). The modified proteins were purified by using CM column or SP column (GE Healthcare), and eluted with a pH gradient of 4.0 to 10.0 to obtain the target component (FIG. 2D).

Example 4: ES and its Variants are High Efficient ATP Enzyme

The sample diluent buffer was prepared from 50 mM HEPES, 1 Mm EDTA and 0.02% $NaN_3$ (pH 7.4). ES, its variant Endu and N-4 were diluted to a final concentration of 500 µg/ml with the sample diluent buffer. Group 1: negative control, the sample diluent buffer added with the same volume of a protein-free buffer; and Group 2, ES, its variant Endu and N-4, with a final concentration of 500 µg/ml.

500 µM ATP was added to the control, and the reaction was performed at water bath at 37° C. for 30 min and then on ice for 5 min to terminate the reaction. The same procedures were also adopted to the samples of ES and its variant at the same time.

The two groups of samples were diluted to appropriate ratio respectively, and then were added to a 96-well ELISA plate successively. The absorbance of the sample in each group was determined by using a Malachite Green Phosphate Assay Kit (BioAssay Systems) and a microplate reader (Multiskan mk3, Thermo Scientific). The concentration of phosphates in the reaction system was calculated and then converted to ATPase activity of ES.

ATPase activity (nM/mg/min)=Δphosphate concentration (nM/ml)/reaction time (30 min)/ES or its variant concentration (mg/ml).

The results showed that ES, Endu and N-4 have high ATPase activity, and the N-4 has the highest ATPase activity.

The same method was used to detect the ATPase activities of mPEG modified ES, Endu and N-4, and the results showed that the ATPase activities of mPEG-ES, mPEG-Endu and mPEG-N-4 are decreased compared with those of ES, Endu and N-4.

All the above experiments adopted Myosin (extracted from pork heart, Sigma) as a positive control, which had been well-known to have high ATPase activity. The results showed that ES and its variant are high efficient ATP enzyme (FIG. 3).

Example 5: ES, Endu and its mPEG Modified Products, Acting as ATPase, can Significantly Decrease the Amounts of ATP in the Whole Cell Homogenate of Human Vascular Endothelial Cells The human vascular endothelial cells was first collected and then prepared into whole cell lysate with cell lysis buffer. The precipitate, impurities and cell debris were removed by centrifugation at low temperature (The above operation was done on the ice at a low temperature). The cell lysate was averagely divided into four groups, and each of them was subjected to a different treatment. Group 1: negative control, added with the same volume of a protein-free buffer; Group 2: treated by ES (50 µg/ml); Group 3: treated by ES (100 µg/ml); Group four: treated by ES (200 µg/ml). Each group was placed at room temperature to allow the reaction to start immediately following the addition of ES, and then was placed back to ice to terminate the reaction after 25 min. The amount of ATP of the cell homogenate in each group was detected by using a ATP bioluminescent detection kit (Sigma-Aldrich). The results showed that, compared with the control group, ES can significantly degraded and reduced the level of ATP in the lysate of of human vascular endothelial cells. The results were consistent with those of example 4 and further demonstrated that ES could also have the ATP degradation activity in a relative complex system such as cell lysis buffer. At the same time, we found that PEG modified ES (mPEG-ES) could also significantly degraded and reduced the level of ATP in the lysate of of human vascular endothelial cells, while the ATP degradation activity of mPEG-ES is only a little lower than that of ES under the circumstances that the doses (50 µg/ml, 100 µg/ml, 200 µg/ml respectively) and treating time of ES and mPEG-ES are same (FIG. 4A).

ES could also be replaced by other proteins with same mechanism or its variant Endu. In the parallel comparison experiment on Endu and mPEG modified Endu (mPEG-Endu) (which is to add 20 kDa mPEG-ALD modification on the ES with additional amino acids MGGSHHHHH (SEQ ID NO:42) on N-terminal), we got the similar results. The whole cell lysis components of human vascular endothelial cells were obtained by the same method mentioned above, and was averagely divided into seven groups with different treatment as followed. Group one: negative control with no treatment; group two: negative control with bovine serum albumin BSA (100 µg/ml), which is a well known protein with no ATPase activity and usually be used for negative control in these kinds of experiments; group three: positive control, treated with pork heart myosin (100 µg/ml), which is a well known protein with high ATPase activity and is used for positive control; group four: treated with ES (100 µg/ml); group five: treated with mPEG-ES (100 µg/ml); group six: treated with Endu (100 µg/ml); group seven: treated with mPEG-Endu (100 µg/ml). Each group was placed at room temperature immediately after adding ES, Endu or mPEG modified products, reacting for 25 min, and was placed back to ice to terminate the reaction. The results showed that when added the same dose myosin, BSA, ES, mPEG-ES, Endu, mPEG-Endu, and under the same reaction condition, myosin showed the highest ATP degradation activity, which also means ATPase activity. ES, mPEG-ES, Endu and mPEG-Endu all showed respective ATPase activity, and among them, ES with natural sequence has the highest ATPase activity and is approximate to myosin; mPEG-ES has the second highest ATPase activity and is slightly lower than ES; Endu and mPEG-Endu have a respectively lower ATPase activity (FIG. 4B).

Example 6: Evaluating ATPase Activity is a Convenient and Accurate Method with High Repeatability for Determining ES Activity The method for determining ATPase activity of ES, variants and PEG modified products thereof was established according to the method mentioned in example 4. ES, mPEG-ES, Endu and mPEG-Endu were diluted into a series of concentration gradients (showed in FIG. 5) with sample diluting buffer on ice bath, respectively. The diluted samples were added to 96-well ELISA plate. OD630 was detected by using Malachite Green Phosphate Assay Kit (Malachite Green Phosphate Assay Kit, Bio Assay System). The concentration of diluted sample was calculated according to the dilution factor. Then, ΔOD630 was calculated according the following formula:

$$\Delta OD630 = S1(OD630) - S2(OD630)$$

Figure 5:
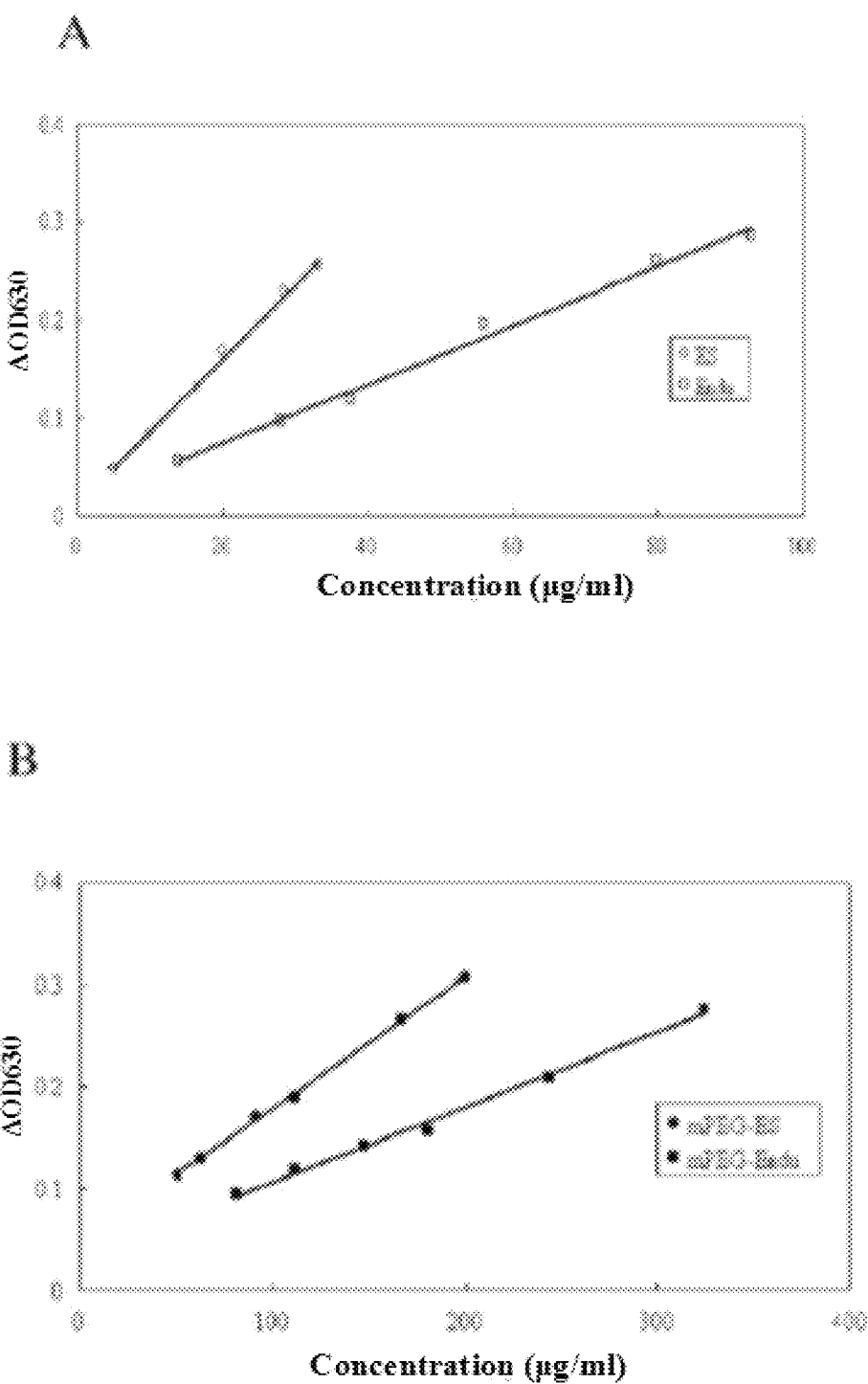
FIG. 5 shows that the ATP enzyme activity assay allows fast and accurate detection of the biological activity of ES, ES variant and their mPEG modified products.
(A) standard curve for detecting the biological activity of ES and Endu based on the ATP enzyme activity assay.
(B) standard curve for detecting the biological activity of mPEG-ES and mPEG-Endu based on the ATP enzyme activity assay.

A curve was plotted with the sample concentrations on the X axis and the corresponding ΔOD630 on the Y axis. Detection and plotting of mPEG-ES, Endu and mPEG-Endu were performed similarly in parallel. The results showed excellent linearity between the sample concentrations and the corresponding ΔOD630 for ES, mPEG-ES, Endu and mPEG-Endu, all with $R^2$ greater than 0.99 (FIG. 5). Thus, within the determined linear range, the method can be widely used for detecting the activity of ES, variants and PEG modified products thereof.

Example 7: Mutation in the ATP Binding Site of ES Results in the Change of ATPase Activity ATPase activity of the ES that has mutation in the ATP binding site was detected using the methods mentioned in example 4. Mutant ES001 has a higher ATPase activity compared with ES, while the activities of mutants ES003-ES008 were dramatically decreased. ATPase activities of mutants ES003-ES008 were similar to that of mouse endostain (MM) (FIG. 6).

Example 8: Mutation in the ATP Binding Site of ES Results in the Change of its ATPase Activity in the Whole Cell Lysate According to the methods mentioned in example 5, the human vascular endothelial cells were collected and whole cell lysate was prepared with the cell lysis buffer. Pellets, impurities and debris in the cell homogenate were removed by centrifuge at low temperature. The whole cell lysate was aliquoted into several groups for different treatments as follows:

Group 1: negative control, treated with equal volume of buffer without ES;

Group 2: treated with ES (100 μg/ml);

Group 3: treated with mouse endostain MM (100 μg/ml);

Group 4: treated with ES mutant ES003 (100 μg/ml);

Group 5: treated with ES mutant ES006 (100 μg/ml);

Group 6: treated with ES mutant ES007 (100 μg/ml);

Group 7: treated with ES mutant ES008 (100 μg/ml).

The amount of ATP in each group was detected using ATP bioluminescent detection kit (Sigma-Aldrich). The results showed that wild type human ES has obvious ATP degradation activity while mouse MM has low ATPase activity since it lacks the typical ATP binding domain ES mutants ES003, ES006, ES007 and ES008 have dramatically decreased ATP degradation activity compared with wild type ES due to the different mutations in the ATP binding site. ES003 and ES008 have the most significant reduction of activity (FIG. 7A).

In another experiment, we also detected ATPase activity of ES mutants ES001, ES004, ES005 in whole cell lysis solution with similar methods. ES001, ES004, ES005 have equal or higher ATPase activity when compared with ES (FIG. 7B).

Example 9: Mutation in the ATP Binding Site Results in the Change of the Endothelial Cell Migration Inhibiting Activity of ES Method for determining cell migration: human microvascular endothelial cells (HMEC, from ATCC) were inoculated into the upper layer of Transwell™ basket (8 μm pore diameter, Costar) containing DMEM (Hyclone) with 1% FBS, $2 \times 10^4$ cells per well. ES of the same concentration (20 μg/ml) was added into both upper layer and bottom layer of the basket. The basket was incubated at 37° C., 5% $CO_2$ for 6 hours to allow the cells to migrate. Then, the cells were fixed with glutaraldehyde and stained with crystal violet. The number of cells completely migrate through the membrane to the bottom layer were counted from 5 fields randomly selected from each hole, and then averaged and compared with the control group to determine the reduction of migrated cells (the inhibition rate of each protein). Each group has three duplications and the experiments were independently repeated at least twice.

The endothelial cells (HMEC) were divided into the following groups for different treatments:

Group 1: negative control, treated with equal volume of buffer without ES;

Group 2: treated with ES (20 μg/ml);

Group 3: treated with mouse endostatin MM (20 μg/ml);

Group 4: treated with ES mutant ES003 (20 μg/ml);

Group 5: treated with ES mutant ES006 (20 μg/ml);

Group 6: treated with ES mutant ES007 (20 μg/ml);

Group 7: treated with ES mutant ES008 (20 μg/ml).

The results showed that the endothelial cell migration inhibiting activity of MM, mutants ES003, ES006, ES007 and ES008 was significantly increased when compared with ES (FIG. 8A).

In another experiment, we also compared the endothelial cell migration inhibiting activity of ES001, ES003, ES004, and ES005 with similar methods. While ES003 showed higher inhibiting activity, other mutants all exhibited lower inhibiting activity when compared with ES (FIG. 8B).

Example 10: Mutation in the ATP-Binding Site Leads to the Change of ATPase Activity and Endothelial Cell Migration Inhibiting Activity of Endu Based on the methods described in examples 4 and 9, ATPase activity (FIG. 9A) and endothelial cell migration inhibiting activity (FIG. 9B) of Endu mutants were compared in this example. The results revealed that the change of ATPase activity and endothelial cell migration inhibiting activity caused by the mutation in ATP-binding site of Endu is similar to the change of corresponding activities of ES caused by mutation of the same type.

Example 11: Mutants with Various Decreases of ATP Activity were Obtained by Mutating the ATP-Binding Motif and the Adjacent Sequence of the Wild Type ES In this example, ATP-binding motif of ES was mutated with two-step PCR, using the cycles and primers described in example 1. Mutation sites were summarized as follows:

| Name | mutation sites | sequence number |
|---|---|---|
| ES010 | MES-R5M | SEQ ID NO. 15 (FIG. 24) |
| ES011 | MES-R5Q | SEQ ID NO. 16 (FIG. 25) |
| ES012 | MES-R5Q&E92Q&P94Q&K96Q | SEQ ID NO. 17 (FIG. 26) |
| S01 | MES-ΔN2-5(HSHR)&Insert S97 | SEQ ID NO. 18 (FIG. 27) |
| S02 | MES-ΔN2-5(HSHR)&Insert T97 | SEQ ID NO. 19 (FIG. 28) |
| S09 | MES-Insert S97 | SEQ ID NO. 20 (FIG. 29) |
| S10 | MES-Insert T97 | SEQ ID NO. 21 (FIG. 30) |
| S12 | MES-ΔC1-4 | SEQ ID NO. 22 (FIG. 31) |
| Z005 | MES-ΔG90&ΔG93&K96Q | SEQ ID NO. 23 (FIG. 32) |
| Z006 | MES-ΔG90&R5Q | SEQ ID NO. 24 (FIG. 33) |
| Z008 | MES-ΔG90&R5Q &ΔG93 | SEQ ID NO. 25 (FIG. 34) |
| Z009 | MES-ΔG90&R5Q&K96Q | SEQ ID NO. 26 (FIG. 35) |
| Z101 | MES-ΔG90&K107R&K118R&K184R | SEQ ID NO. 27 (FIG. 36) |
| Z103 | ES008-K76R&K107R &K184R | SEQ ID NO. 28 (FIG. 37) |
| Z104 | ES008-K76R&K118R &K184R | SEQ ID NO. 29 (FIG. 38) |
| ZN1 | Z101-K76 | SEQ ID NO. 30 (FIG. 39) |
| ZN2 | MES-G90A&K76R&K107R&K118R&K184R | SEQ ID NO. 31 (FIG. 40) |
| ZN3 | ZN2-G93A | SEQ ID NO. 32 (FIG. 41) |
| ZN4 | ZN2-A90P | SEQ ID NO. 33 (FIG. 42) |

ATPase activity of ES variants, mutants and the mPEG modified products thereof in examples 2 and 11 were measured with the method described in example 4, and the results were shown in Table 1.

TABLE 1

| Number | Sample | ATPase activity (nM/mg/min) | Sample | ATPase activity (nM/mg/min) |
|---|---|---|---|---|
| 1 | ES | 14804 | mPEG-ES | 2664 |
| 2 | Endu | 5353 | mPEG-Endu | 1641 |
| 3 | N-4 | 25448 | mPEG-N-4 | 13555 |
| 4 | MM | 2856 | mPEG-MM | 277 |
| 5 | ES001 | 16361 | mPEG-001 | 5359 |
| 6 | ES003 | 5200 | mPEG-003 | 1116 |
| 7 | ES004 | 5585 | mPEG-004 | 570 |
| 8 | ES005 | 4038 | mPEG-005 | 1097 |
| 9 | ES006 | 4069 | mPEG-006 | 773 |
| 10 | ES007 | 7137 | mPEG-007 | 3059 |
| 11 | ES008 | 4250 | mPEG-008 | 1957 |
| 12 | ES010 | 8809 | mPEG-010 | 2561 |
| 13 | ES011 | 4764 | mPEG-011 | 1191 |
| 14 | ES012 | 451 | mPEG-012 | 113 |
| 15 | S01 | 10202 | mPEG-S01 | 7010 |
| 16 | S02 | 2283 | mPEG-S02 | 2066 |
| 17 | S09 | 1876 | mPEG-S09 | 723 |
| 18 | S10 | 1465 | mPEG-S10 | 646 |
| 19 | S12 | 1500 | mPEG-S12 | 200 |
| 20 | Z005 | 10400 | mPEG-Z005 | 5706 |
| 21 | A006 | 533 | mPEG-Z006 | 79 |
| 22 | Z008 | 424 | mPEG-Z008 | 382 |
| 23 | Z009 | 10495 | mPEG-Z009 | 5389 |
| 24 | Z101 | 5434 | mPEG-Z101 | 2439 |
| 25 | Z103 | 1473 | mPEG-Z103 | 499 |
| 26 | Z104 | 3192 | mPEG-Z104 | 1919 |
| 27 | ZN1 | 7402 | mZN1 | 2211 |
| 28 | ZN2 | 6227 | mZN2 | 2448 |
| 29 | ZN3 | 5319 | mZN3 | 3672 |
| 30 | ZN4 | 4157 | mZN4 | 2450 |

Example 12: The Effect of ES Mutant on HMEC Migration

Cell migration assays were estimated with the Transwell Assay described in example 9. Considering that endothelial cell migration inhibiting activities of many mutant proteins were significantly enhanced, decreased dose (5 μg/mL) was selected to treat cells in this example to show the differences between activities of various mutant proteins more significantly, however, significant inhibitory effects were also observed, as shown in FIGS. 43-47. Except Z103, Z104, ZN3 and ZN4, of which both ATPase activity and endothelial cell migration inhibiting activity were reduced compared with ES, all other mutants showed equal or significantly increased endothelial cell migration inhibiting activity, which is consistent with the negative correlation between ATPase activity and endothelial cell migration inhibiting activity. The exception of the four mutants Z103, Z104, ZN3 and ZN4 may be caused by the effect of overmuch mutation sites on the protein integral structure.

Example 13: The Inhibitory Effect of Endostatin Mutants on Tumor Growth of Non-Small Lung Cancer A549 Cells at Animal Level Proliferating A549 cells (ATCC CCL-185) were cultured and subcutaneously injected into 6 to 8-week nude mice (Vital River Laboratory Animal Technology Co. Ltd.) at. Drug treatment was started when 80-100 mm³ tumor volume was achieved. Tumor-bearing mice were divided into five groups and treated with different administration respectively. In view of the increased anti-angiogenesis activity of mutants, a lower dose (12 mg/kg, common dose was 24 mg/mL) was administered to treat tumor-bearing mice. Group 1: negative control group without drug treatment, only saline at equal dose was injected; Group 2: mPEG-ES administration group; Group 3: M003 administration group, M003 was administered; Group 4: M007 administration group, M007 was administered; Group 5: MZ101 administration group, MZ101 was administered. The four Endostatin mutant above, i.e. mPEG-ES, M003 (mPEG-ES003), M007(mPEG-ES007) and MZ101 (mPEG-Z101) were all injected in caudal vein once a week at a dose of 12 mg/kg, the treatment time was 21 days (three weeks). During the experiment, long radius A and short radius B of tumors in every group were measured with Electronic Vernier caliper and tumor volumes were calculated through the formula V=0.5×A×B²(mm³).

Tumor growth results, shown in FIG. 48A, revealed that compared with negative control (Group 1), tumor volume inhibition rate of mPEG-ES administration (Group 2) was 45%; tumor volume inhibition rates of M003 administration (Group 3) and M007 administration (Group 4) were approximately equal to mPEG-ES administration; tumor volume inhibition rate of MZ101 administration (Group 5) was 71.2%, which group has the smallest tumor volume and the highest drug inhibition rate.

Once the experiment ended up, tumor was dissected from the tumor-bearing mice and weighed. As shown in FIG. 48B, tumor weight inhibition rate of every drug treatment group was accordant with the tumor volume results. Compared with negative control, tumor weight inhibition rate of MS03 administration (group 2) was 42%; tumor weight inhibition rate of M003 administration (group 3) and M007 administration (group 4) were approximately equal to mPEG-ES administration; tumor volume inhibition rate in MZ101 administration (group 5) was 64%, which group has the smallest tumor weight and the highest drug inhibition rate.

Results in this example demonstrated that Endostatin mutants had favorable tumor growth inhibition effects at the dose of 12 mg/kg/week in tumor-bearing mice model. The inhibition rate of mPEG-ES was about 40%; the inhibition rates of M003 and M007 were approximately equal to and slightly lower than mPEG-ES; the inhibition effect of MZ101 was better than mPEG-ES, displaying the best curative effect and the highest tumor inhibition rate (about 60-70%).

The invention claimed is:

1. A method of tumor therapy comprising administering to a subject having a tumor a mutant of human endostatin having the amino acid sequence set forth in SEQ ID NO:1 or of a human endostatin variant having the amino acid sequence set forth in SEQ ID No:2, 3 or 4, wherein said mutant has increased anti-angiogenesis activity as compared with the corresponding wild type endostatin or a variant thereof, wherein said mutant has decreased ATPase activity as compared with the corresponding wild type endostatin or a variant thereof, and wherein said mutant is selected from the group consisting of
   a) a mutant having the amino acid sequence set forth in SEQ ID NO:6,
   b) a mutant having the amino acid sequence set forth in SEQ ID NO:10,
   c) a mutant having the amino acid sequence set forth in SEQ ID NO:27, and
   d) a mutant having the amino acid sequence set forth in SEQ ID NO:30.

2. The method of claim 1, wherein said mutant is further covalently linked to a PEG molecule.

3. The method of claim 2, wherein the molecular weight of said PEG is 5-40 kD.

4. The method of claim 3, wherein said PEG is covalently linked to the α amino group at N-terminal of said mutant.

5. The method of claim 4, wherein said PEG is Monomethoxy Poly(ethylene glycol).

6. The method of claim 5, wherein said Monomethoxy Poly(ethylene glycol) is Monomethoxy Poly(ethylene glycol)-Aldehyde (mPEG-ALD).

* * * * *